(12) United States Patent
Matsue et al.

(10) Patent No.: US 8,254,649 B2
(45) Date of Patent: Aug. 28, 2012

(54) MEDICAL IMAGE OBSERVATION SYSTEM

(75) Inventors: Kenji Matsue, Nasushiobara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 898 days.

(21) Appl. No.: 12/173,274

(22) Filed: Jul. 15, 2008

(65) Prior Publication Data

US 2009/0022377 A1    Jan. 22, 2009

(30) Foreign Application Priority Data

Jul. 17, 2007  (JP) ................................. 2007-185896

(51) Int. Cl.
*G06K 9/00*  (2006.01)
(52) U.S. Cl. ...................................................... 382/128
(58) Field of Classification Search ........... 382/100–150
See application file for complete search history.

(56) References Cited

U.S. PATENT DOCUMENTS

| | | | | |
|---|---|---|---|---|
| 5,779,634 A * | 7/1998 | Ema et al. | ...................... | 600/407 |
| 7,640,171 B2 * | 12/2009 | Gendron et al. | .................. | 705/2 |
| 7,793,217 B1 * | 9/2010 | Kim et al. | ...................... | 715/255 |
| 7,818,041 B2 * | 10/2010 | Kim et al. | ...................... | 600/407 |
| 7,933,782 B2 * | 4/2011 | Reiner | .............................. | 705/2 |
| 2005/0226405 A1 | 10/2005 | Fukatsu et al. | | |
| 2007/0109402 A1 | 5/2007 | Niwa | | |

FOREIGN PATENT DOCUMENTS

| | | |
|---|---|---|
| CN | 1969744 A | 5/2007 |
| JP | 5-81156 | 4/1993 |
| JP | 2003-135427 | 5/2003 |

OTHER PUBLICATIONS

Japanese Office Action mailed on May 22, 2012, issued for JP Application No. 2007-185896.

* cited by examiner

*Primary Examiner* — Dixomara Vargas
(74) *Attorney, Agent, or Firm* — Oblon, Spivak, McClelland, Maier & Neustadt, L.L.P.

(57) ABSTRACT

The report storage stores an interpretation report that includes patient-identifying information, examination-specifying information, and medical image-specifying information that specifies medical image data. The image data storage stores the medical image data that includes image data and additional information for the image data that includes the patient-identifying information, the examination-specifying information, and the medical image-specifying information. The key image-searching part specifies an interpretation report that includes patient-identifying information specified by a display request for the medical image data and specifies the medical image data using the medical image-specifying information included in the specified interpretation report. The image data-searching part reads the medical image data from the image data storage based on the additional information of the specified medical image data and the display request. The displaying part displays a medical image based on the read medical image data.

9 Claims, 12 Drawing Sheets

FIG. 7

⟨UPPER LIMIT OF READABLE NUMBER OF CT IMAGES⟩

| | | SPEED OF COMMUNICATION PATH | | |
|---|---|---|---|---|
| | | 10Mbps OR LESS | 100Mbps ~1Gbps | 1Gbps OR MORE |
| AMOUNT OF MEMORY | 512MB OR LESS | 100 | 400 | 400 |
| | 512MB ~1GB | 100 | 800 | 800 |
| | 1GB OR MORE | 100 | 1000 | 1600 |

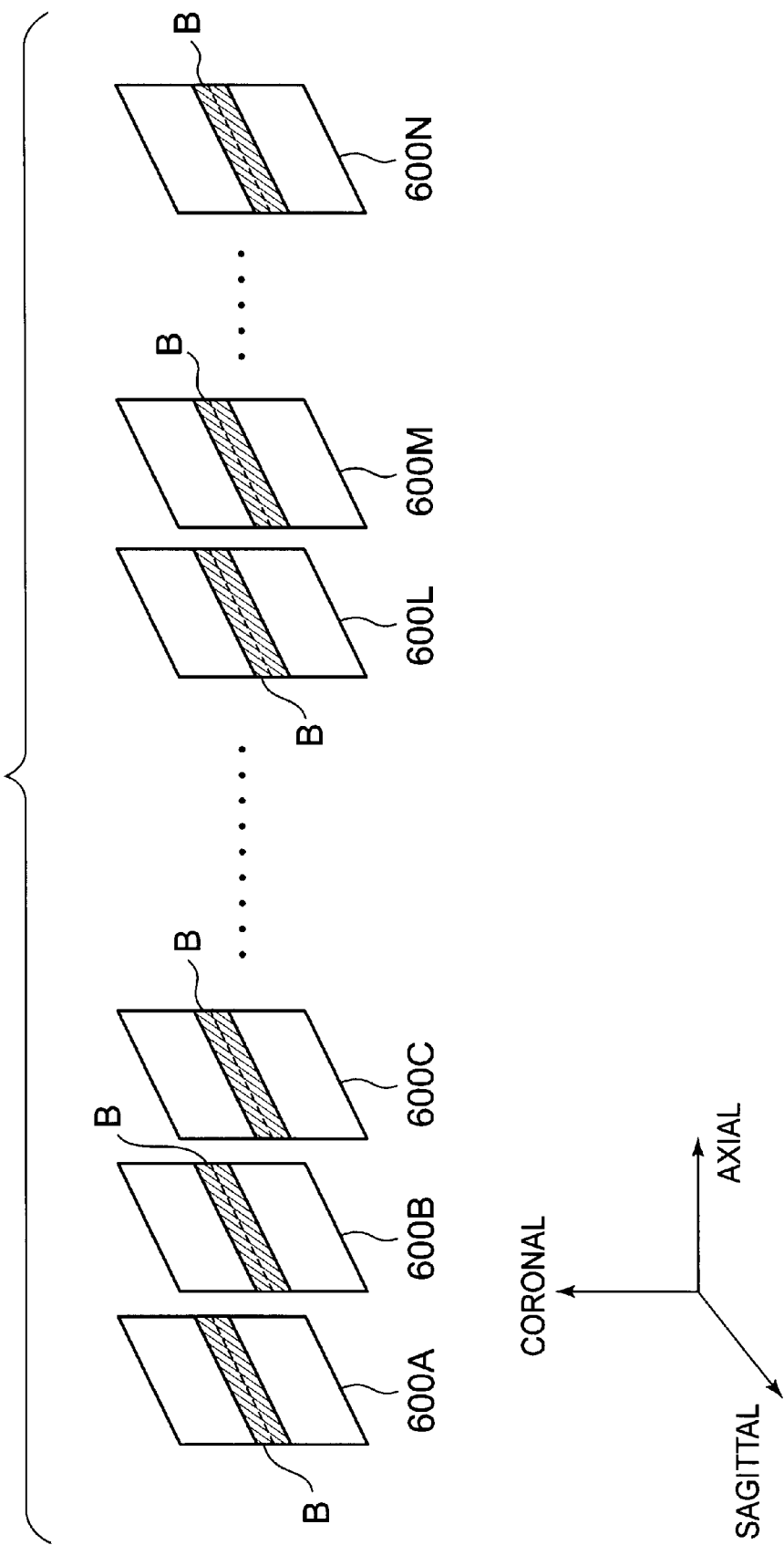

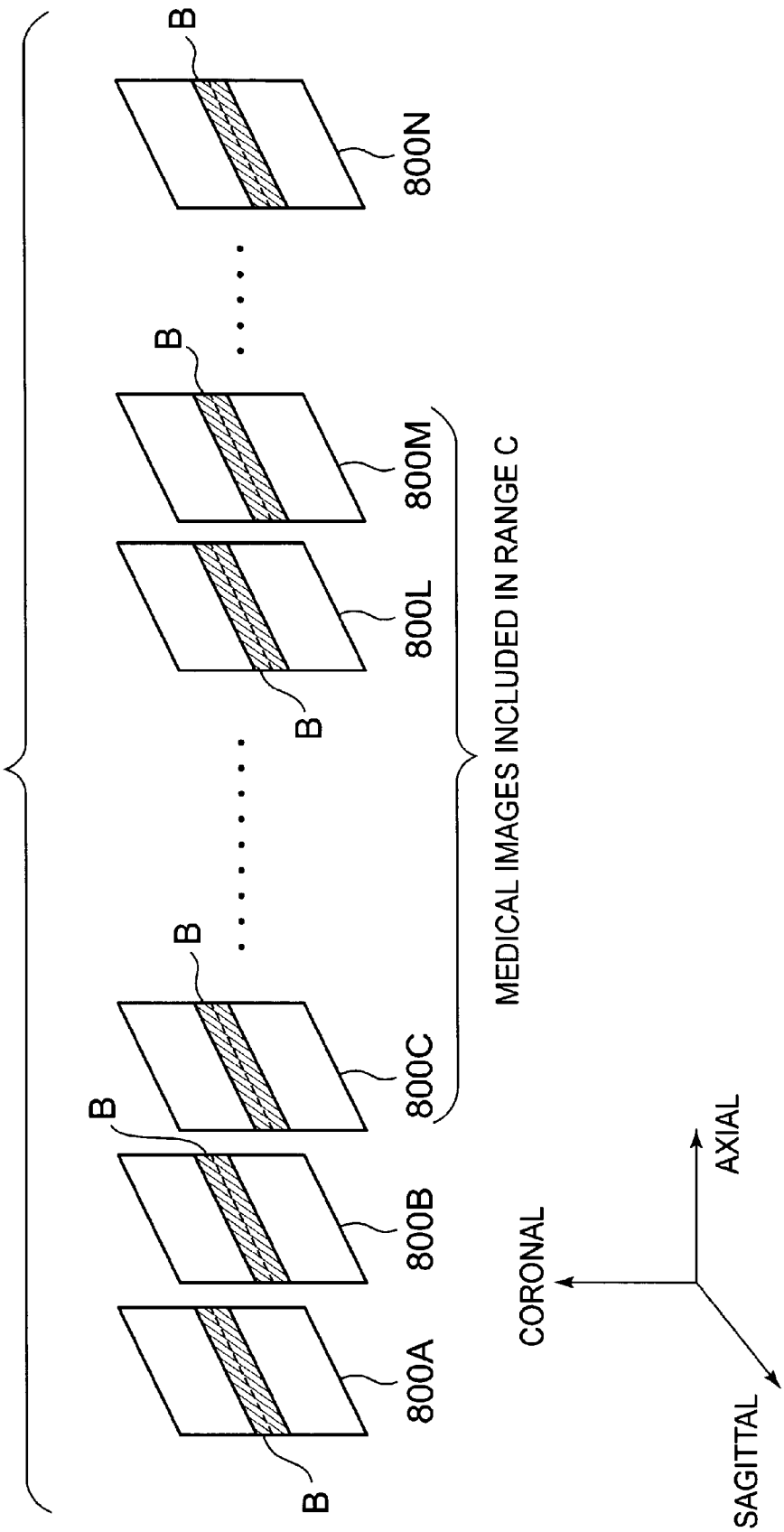

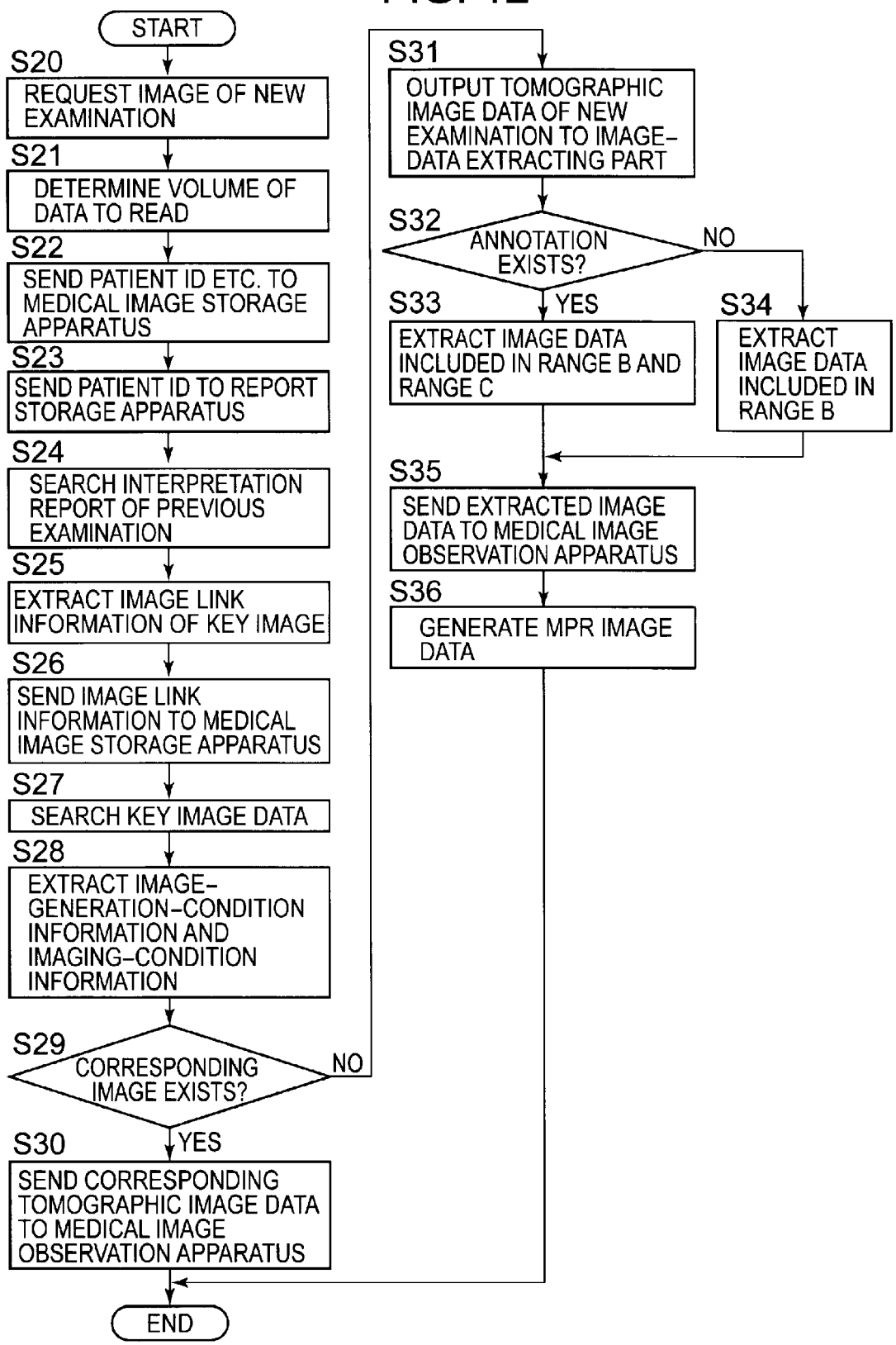

MEDICAL IMAGE OBSERVATION SYSTEM

BACKGROUND OF THE INVENTION

1. Field of the Invention

The present invention relates to a medical image observation system that displays medical image data acquired by a medical image acquisition apparatus. In particular, the present invention relates to a medical image observation system that generates medical image data associated with medical image data that was generated in a previous examination.

2. Description of the Related Art

Medical image data acquired by a medical image acquisition apparatus such as an X-ray CT (X-ray Computed Tomography) apparatus and an MRI (Magnetic Resonance Imaging) apparatus is managed in a picture archiving and communication system (PACS) connected via a network. This picture archiving and communication system (PACS) is connected via a network to a hospital information system (HIS) and a radiology information system (RIS). An operator such as a physician can interpret a medical image by reading desired medical image data from a picture archiving and communication system using a client terminal on the network (Japanese Published Unexamined Application No. 1993-81156).

Furthermore, a plurality of sets of medical image data acquired by the medical image acquisition apparatus are classified for each patient according to the DICOM (Digital Imaging and Communication in Medicine) specification, and the classification by patient is further classified per examination. The examination consists of a series of medical image data. The series includes a plurality of sets of medical image data. The classification of a plurality of sets of medical image data with such a structure shows that, with the patient assumed to be at the top level, a specific examination is performed on the patient, the examination consists of a series of medical image data, and the series includes a plurality of sets of medical image data.

In a client terminal, a medical image acquired in an examination newly performed on a patient (hereinafter may be referred to as "new examination") and a medical image acquired in an examination performed in the past (hereinafter may be referred to as "previous examination") for a patient may be compared and interpreted. In this case, the client terminal inclusively reads all medical image data included in the series of the new examination from the picture archiving and communication system, and generates a medical image to be compared with the medical image of the previous examination based on all of the medical image data.

For example, when MPR (Multi Planar Reconstruction) processing is performed on medical image data acquired in a previous examination, image data (MPR image data) on an arbitrary cross-section generated through MPR process is stored in the medical image storage system. Additionally, if the MPR image generated in the previous examination is compared and interpreted with an MPR image of a new examination, it is necessary to generate MPR image data based on a plurality of sets of medical image data acquired in the new examination. For example, by generating MPR image data of the new examination that has the same segment of the cross-section as the MPR image of the previous examination, the MPR image of the previous examination and the MPR image of the new examination are compared and interpreted.

To generate MPR image data of a new examination on the client terminal, all medical image data acquired in the new examination is conventionally imported into the client terminal from the picture archiving and communication system. MPR image data to be compared is then generated on the client terminal based on a plurality of sets of read medical image data.

As stated above, when a medical image of a new examination and a medical image of a previous examination are compared and interpreted on the client terminal, all medical image data of the new examination is conventionally imported into the client terminal from the picture archiving and communication system. For example, when an MPR image of a previous examination and an MPR image of a new examination are compared and interpreted, all medical image data included in the new examination is imported into the client terminal from the picture archiving and communication system in order to generate an MPR image of the new examination on the client terminal.

However, with the method of the related art, the volume of medical image data that is sent to the client terminal from the picture archiving and communication system is so large that it is necessary to install large-capacity memory on the client terminal. In particular, when medical image data is imported into a general-use personal computer for comparison and interpretation, the volume of medical image data to be read is also limited, because the capacity of the memory is limited. Therefore, it is possible that the medical image data that is necessary for interpretation will not be sufficiently read.

Moreover, because the volume of medical image data that is sent to the client terminal from the picture archiving and communication system is large, the amount of time required for importing it into the client terminal increases. Thereby, the time necessary for interpretation increases, resulting in a difficulty to make a diagnosis efficiently.

Moreover, there is a desire to import medical image data included in a plurality of series from the picture archiving and communication system into the client terminal in order to compare and view it. In such a case, all medical image data included in each series is conventionally imported into the client terminal from the picture archiving and communication system. Therefore, a problem arises in which large-capacity memory is needed on the client terminal, resulting in an increase in time for reading. Therefore, it is difficult to make a diagnosis efficiently in this case as well.

SUMMARY OF THE INVENTION

The present invention has been devised to provide a medical image observation system that can efficiently read and display desired medical image data when viewing a medical image.

The first aspect of the present invention is a medical image observation system comprising: a report storage configured to store an interpretation report that at least includes patient-identifying information, examination-specifying information, and medical image-specifying information that specifies medical image data; a medical image storage configured to store medical image data that includes image data and additional information regarding said image data that at least includes patient-identifying information, examination-specifying information, and medical image-specifying information; a medical image data-specifying part configured to specify an interpretation report that includes patient-identifying information based on said patient-identifying information specified by a display request for medical image data and to specify medical image data using the medical image-specifying information included in said specified interpretation report; a medical image data-reading part configured to read medical image data from said medical image storage based on the additional information of said specified medical image data and the examination-specifying information specified by said display request; and a displaying part configured to display an image based on the image data included in said read medical image data.

According to this first aspect, by reading medical image data based on additional information of medical image data specified by medical image-specifying information included in a specified interpretation report and examination-specifying information specified by a display request of the medical image data, the desired medical image data can be read and displayed sufficiently.

Moreover, the second aspect of the present invention is the medical image observation system related to the first aspect wherein said medical image storage is configured to store said medical image data so that image-generating conditions that show the conditions under which said image data has been generated are included in said additional information, said medical image data-reading part comprising: an image-generating condition-extracting part configured to extract the image-generating conditions from the additional and an information of said specified medical image data; image-generator configured to read the medical image data from said medical image storage based on the patient-identifying information and the examination-specifying information specified by said display request, so as to generate new medical image data by performing image processing on the image data included in said read medical image data according to said extracted image-generating conditions, and said displaying part is configured to display an image based on the image data included in said new medical image data.

According to this second aspect, by applying image processing to the read medical image data according to the image-generating conditions of the specified medical image data, the desired medical image data can be generated and displayed efficiently.

Moreover, the third aspect of the present invention is the medical image observation system related to the first aspect wherein said medical image storage is configured to store the medical image data so that the image-generating conditions that include information that shows the position in the subject at which said image data has been acquired are included in said additional information, said medical image data-reading part is configured to extract the image-generating conditions from the additional information of said specified medical image data and to read medical image data included in a predetermined range that includes the position at which said specified medical image data has been acquired among a plurality of sets of medical image data specified based on the patient-identifying information and the examination-specifying information specified by said display request, and said displaying part is configured to display an image based on the image data included in said read medical image data.

According to this third aspect, by reading the medical image data included in the predetermined range including the position at which the specified medical image data was acquired among a plurality of sets of medical image data stored in the medical image storage, the desired medical image data can be read and displayed efficiently.

BRIEF DESCRIPTION OF THE DRAWINGS

FIG. 7 is a table illustrating the capacity of image data that the medical image observation apparatus can read.

FIG. 9 is a diagram illustrating a frame format for describing a range in which image data is extracted from medical image data of the new examination.

FIG. 11 is a diagram illustrating a frame format for describing a range in which image data is extracted from medical image data of the new examination.

FIG. 12 is a flow chart illustrating a sequence of processes of the medical image observation system according to the second embodiment of the present invention.

DETAILED DESCRIPTION OF THE EMBODIMENTS

First Embodiment

Figure 1:
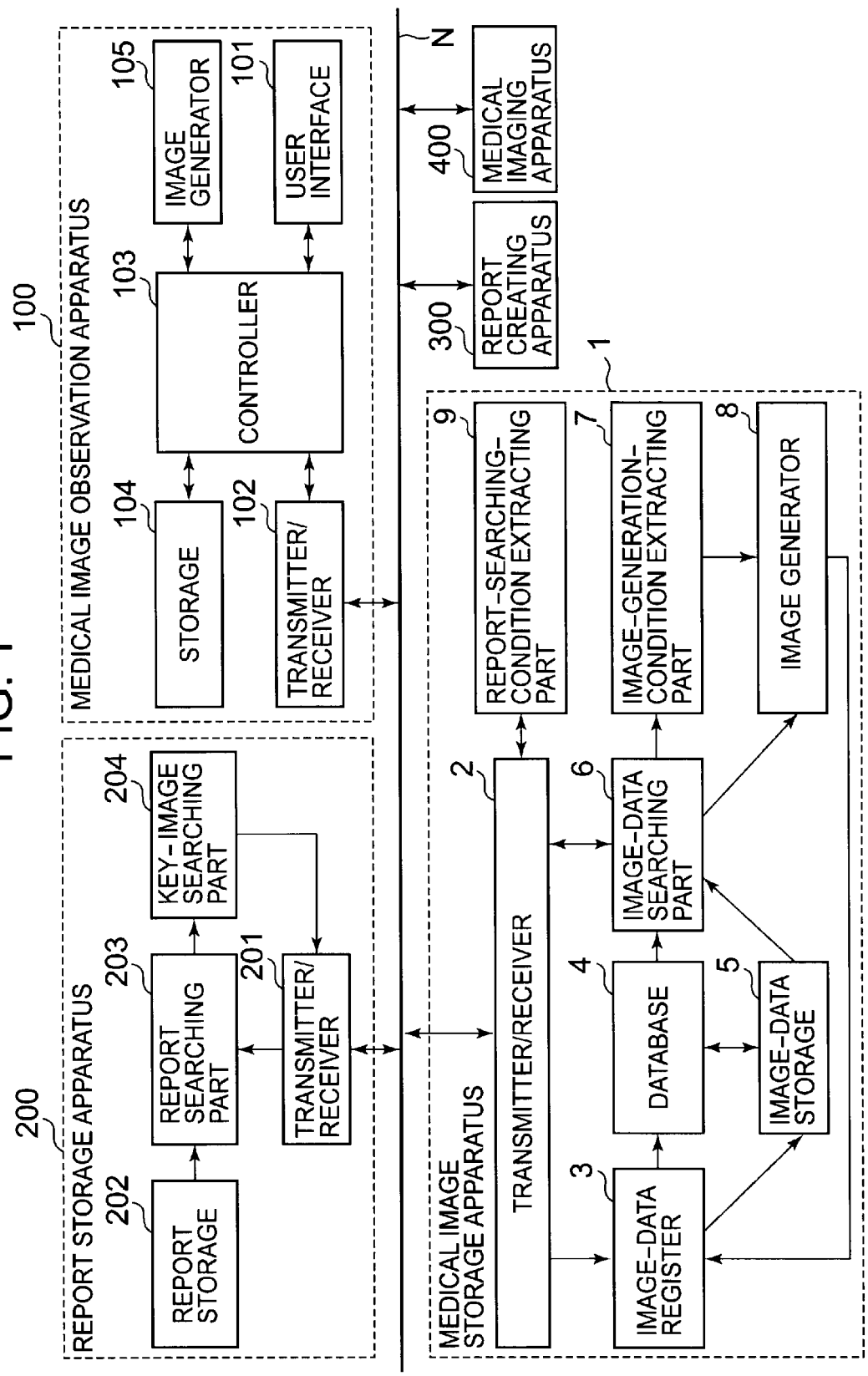
FIG. 1 is a block diagram illustrating a medical image observation system according to the first embodiment of the present invention.

A medical image observation system according to a first embodiment of the present invention is described with reference to FIG. 1. FIG. 1 is a block diagram illustrating the medical image observation system according to the first embodiment of the present invention.

As shown in FIG. 1, in an in-hospital system, a medical image storage apparatus (medical image server) 1, a medical image observation apparatus (client terminal) 100, a report storage apparatus (report server) 200, a report-creating apparatus 300, and a medical image-imaging apparatus 400 are connected via a network N.

The medical image storage apparatus 1 is provided with a computer that has a communication function and can communicate data via the network N. The medical image storage apparatus 1 has a management function that notifies of registration of medical image data and a storage destination of the medical image data and stores medical image data in a plurality of image storage apparatuses in order to manage the medical image data.

The medical image-imaging apparatus 400 acquires medical image data by creating an image of the inside of a subject. The medical image-imaging apparatus 400 includes an ultrasound diagnosis apparatus that visualizes the inside of a subject by transmitting ultrasound, an X-ray diagnosis apparatus or an X-ray CT apparatus that visualizes the inside of a subject by irradiating X-rays, or an MRI apparatus that visualizes the inside of a subject by generating a magnetic field or the like. The medical image-imaging apparatus 400 is provided with a computer that has a communication function and can communicate data via the network N. For example, the medical image-imaging apparatus 400 acquires a plurality of sets of 2-dimensional image data (tomographic image data) along an arbitrary direction in a subject. The first embodiment, as an example, describes a case in which the medical image-imaging apparatus 400 acquires a plurality of sets of tomographic image data along an arbitrary direction in a subject.

This in-hospital system is established using an in-hospital LAN (Local Area Network) installed in a medical institution such as a hospital. The in-hospital system then communicates medical image data and additional information thereof according to the DICOM specification.

The medical image-imaging apparatus 400 outputs the medical image data with the additional information added. Here, the medical image data with the additional information added is referred to as "DICOM image data." The additional information comprises, according to the DICOM specification, information regarding the examination date and time, information regarding a patient name, patient ID, examination ID, series ID, image ID, which is identification information specific to a medical image, information regarding imaging conditions, information regarding image-generating conditions, and attribute information regarding an image. Furthermore, DICOM image data corresponds to an example of the "medical image data" according to the present invention.

Moreover, patient ID corresponds to the "patient-identifying information" according to the present invention, examination ID corresponds to the examination-specifying information according to the present invention, and image ID corresponds to the "medical image-specifying information" according to the present invention.

Information such as information regarding a patient's name, patient ID, examination ID, series ID, image ID, information regarding imaging conditions, information regarding image-generating conditions, and attribute information regarding an image are standardized according to the DICOM specification. Information regarding a patient's name is information that shows the name of a patient for whom imaging data has been captured. Patient ID is information that specifies the patient who has undergone imaging. Examination ID is information for specifying the details of an examination. Series ID is information that is used to classify medical image data, including the site of the imaging, the time at which an image was generated, the slice thickness, use of a contrast medium, etc.

If a plurality of examinations has been performed on a patient, an examination ID that shows each examination ID is assigned to the medical image data acquired in each examination in order to classify each examination. Moreover, if a plurality of sites has been imaged and a plurality of series is included in an examination, a series ID that shows each series is assigned to the medical image data acquired for each series in order to classify each series. Specifically, a plurality of sets of medical image data with a specific patient ID assigned is classified per examination with examination ID and each examination is classified per series with series ID.

Information regarding imaging conditions is information that shows the imaging conditions by the medical image-imaging apparatus 400. For example, information regarding imaging conditions includes information regarding an imaging site that shows the site of a patient who has undergone imaging and information regarding an imaging position (coordinate information) that shows the position at which the medical image data was captured. Information regarding an imaging site is information that shows a site such as a chest area or an abdominal area of a patient. For information regarding an imaging position (coordinate information), for example, a predetermined position of a bed in the medical image-imaging apparatus 400 is defined as the reference position.

Information regarding image-generating conditions is information that shows the conditions under which medical image data has been generated. As an example, information regarding image-generating conditions of tomographic image data (2-dimensional image data) will be described. Information regarding image-generating conditions includes information such as information regarding a cross-sectional position (cross-sectional coordinate information) that shows a position of a cross-section in a subject at which tomographic image data has been generated. Information regarding image-generating conditions further includes directional information that shows the direction of tomographic image, thickness information that shows the thickness of a tomographic image, and information regarding image processing that shows details of image processing that has been performed, etc. For information regarding a cross-sectional position (cross-sectional coordinate information), for example, a predetermined position of a bed in the medical image-imaging apparatus 400 is defined as the reference position. Moreover, directional information shows the direction of the tomographic image, that is the direction in which the tomographic image was captured or the direction in which the tomographic image has been generated. Image processing includes processing such as MPR processing, MIP (Maximum Intensity Projection) processing, or Min IP (Minimum Intensity Projection) processing. For example, if generated medical image data is MPR image data generated in a specific 2-dimensional cross-section, the information regarding image-generating conditions includes information such as information regarding a cross-sectional position (cross-sectional coordinate information) that shows the position of the cross-section at which the MPR image has been generated, directional information that shows the direction of the MPR image, and thickness information that shows the thickness of the MPR image.

The MPR image data is generated, for example, by a belowmentioned medical image observation apparatus 100 or an image-generating apparatus such as a 2D workstation or a 3D workstation, which is not shown in the figure. The information regarding image-generating conditions is then added to the MPR image data as additional information in the medical image observation apparatus 100 or the image-generating apparatus.

Attribute information regarding an image is information for specifying the type of medical image. Attribute information regarding an image corresponds, for example, to the name of the medical equipment, a station name, a manufacturer model name, the manufacturer of the medical equipment, an institution name, the name of an implementation version, the type of image, the AE title, the software version, SOP class UID, the name of protocol, the serial number of the apparatus, or information that specifies the site of an examination, etc.

The medical image observation apparatus 100 receives medical image data included in a desired patient, a desired examination, or a desired series from the medical image storage apparatus 1 in order to cause a displaying apparatus to display a medical image.

Figure 2:
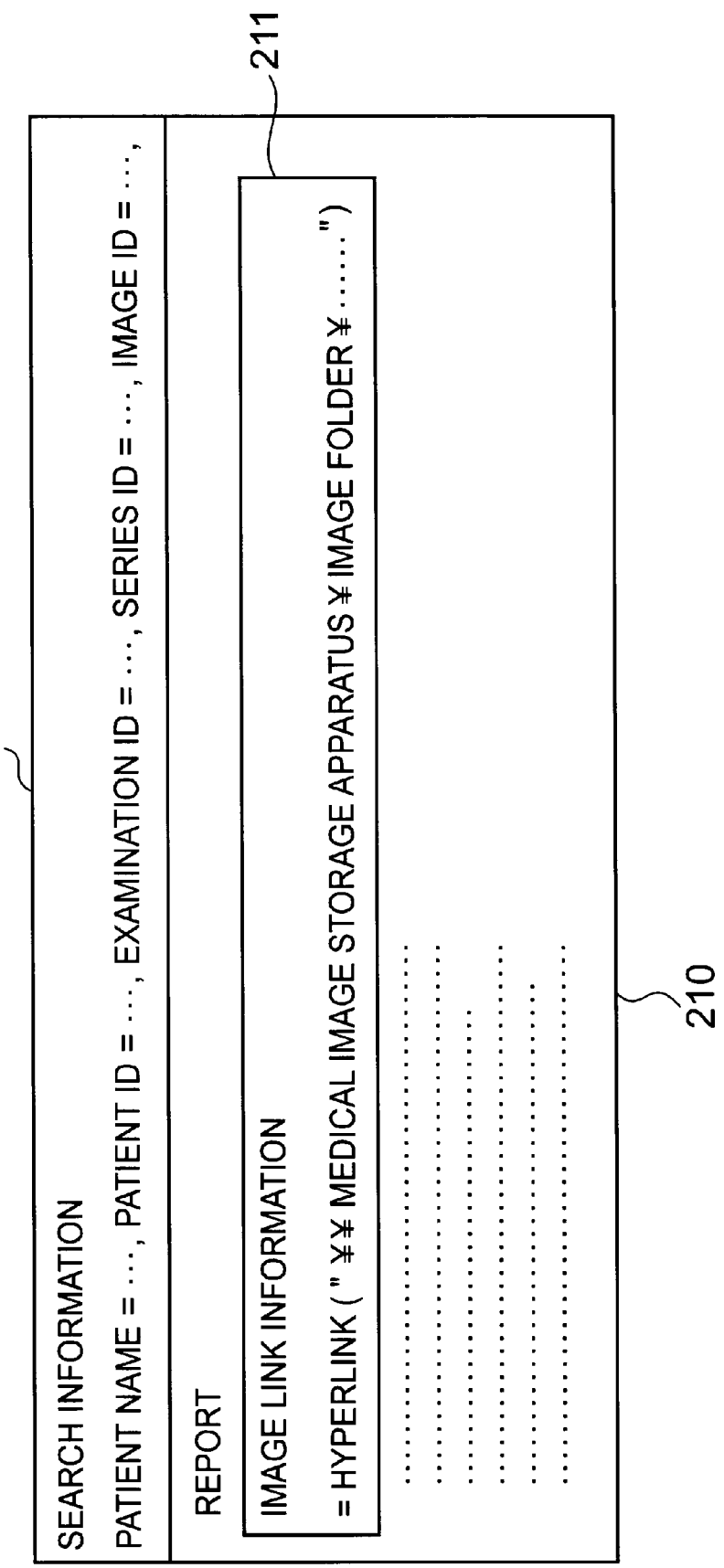
FIG. 2 is a diagram illustrating the data structure of an interpretation report.

The report storage apparatus 200 stores an interpretation report. An interpretation report is a report created by a physician who makes the interpretation, etc. A physician, etc., interprets a medical image obtained in an examination, etc. and describes details of the interpretation in an interpretation report. Here, a data structure of an interpretation report is described with reference to FIG. 2. FIG. 2 is a diagram illustrating the data structure of an interpretation report. As shown in FIG. 2, an interpretation report is constituted with retrieval information 212 added to a report 210.

The report 210 is data of a document style and includes a text that shows details of the report such as observations and diagnosis. Image link information 211 (hyperlink) that shows the location of the referred medical image is embedded into the report 210. The medical image referred when creating the report may be referred to as a "key image" below. The image link information 211 links the text in the report 210 with a path on the network N. This path shows a location where the medical image is stored in the interpretation report (information regarding a storage position). Furthermore, the "key image" in the present embodiment corresponds to an example of the "medical image data specified by medical image-specifying information included in a specified interpretation report" of the present invention.

The retrieval information 212 is information that shows attributes of the interpretation report. Similarly to additional information added to a medical image, the retrieval information 212 includes information regarding the examination date and time, information regarding a patient's name that shows the patient's name of a patient for the interpretation report, patient ID, examination ID that shows the examination for which the interpretation report has been created, and image ID that shows ID of the medical image (key image) in the report, etc.

The report-creating apparatus 300 supports to create an interpretation report. In response to the input of observations and diagnosis using an input apparatus, the report-creating apparatus 300 arranges text to generate data of the report 210 by. In addition, the report-creating apparatus 300 creates the image link information 211 and adds the retrieval information 212 to the report 210.

Furthermore, an image-generating apparatus such as a 2D workstation or a 3D workstation, which is not shown in the figure, may be connected to the network N. This image-generating apparatus generates medical image data such as 3-dimensional image data or MPR image data (image data on an arbitrary cross-section) by performing image processing, such as rendering, on medical image data acquired by the medical image-imaging apparatus 400.

Furthermore, in this first embodiment, image processing such as rendering processing or MPR processing may be performed on the medical image observation apparatus 100 by giving the medical image observation apparatus 100 an image processing function.

In this first embodiment, the medical image storage apparatus 1, the medical image observation apparatus 100, and the report storage apparatus 200 comprise an example of the medical image observation system of the present invention.

(Outline of Processes)

Figure 3:
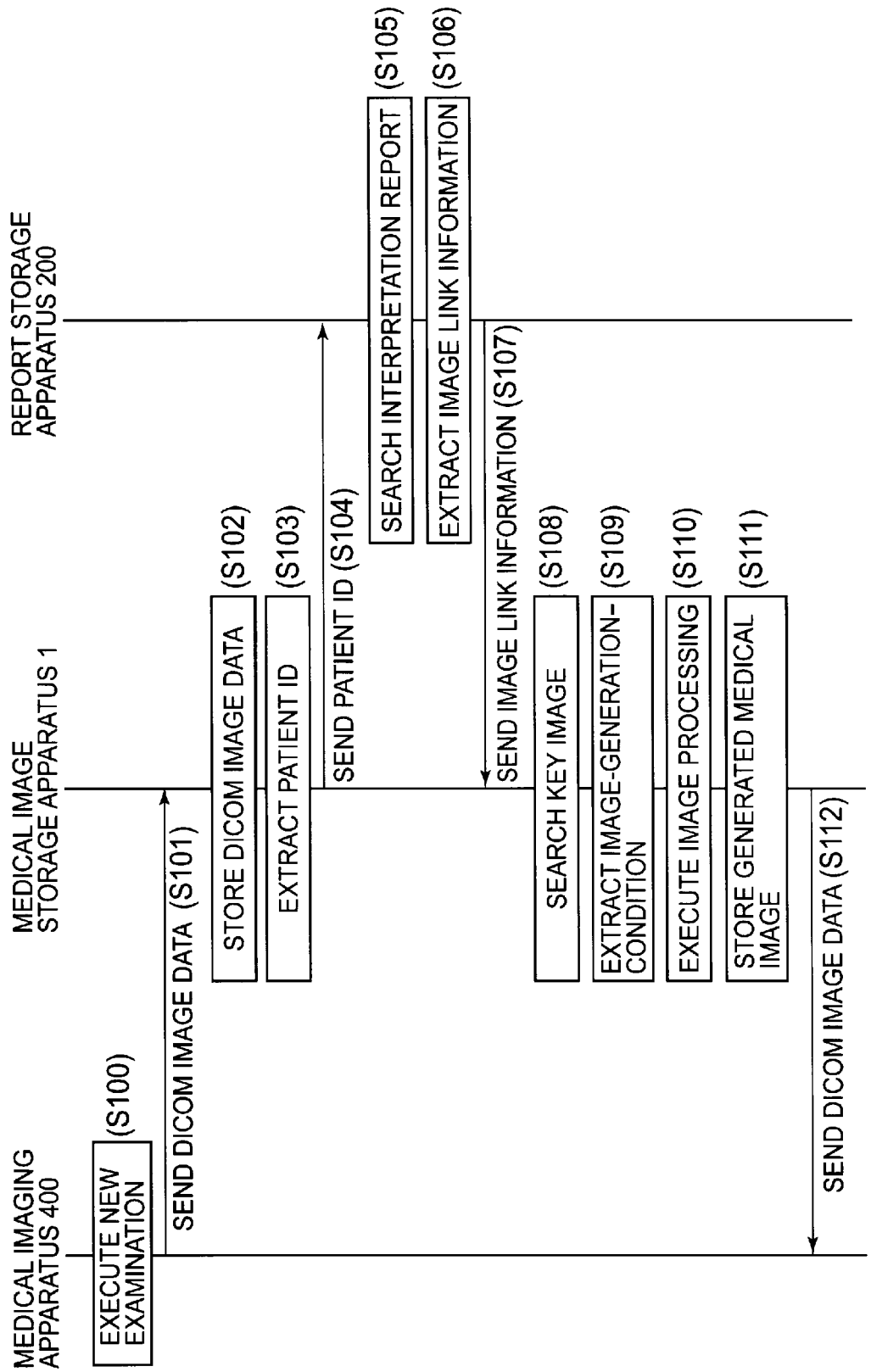
FIG. 3 is a sequence diagram illustrating the outline of processes of the medical image observation system according to the first embodiment of the present invention.

Here, the outline of processes of the medical image observation system according to the first embodiment is described with reference to FIG. 3. FIG. 3 is a sequence diagram illustrating the outline of processes of the medical image observation system according to the first embodiment of the present invention.

Firstly, DICOM image data of a new examination is generated by conducting a new examination in a patient in the medical image-imaging apparatus 400 (Step S100). The medical image-imaging apparatus 400 sends the DICOM image data of the new examination to the medical image storage apparatus 1 (Step S101).

The medical image storage apparatus 1 stores the DICOM image data of the new examination (Step S102). The medical image storage apparatus 1 extracts patient ID added to the DICOM image data of the new examination (Step S103). The medical image storage apparatus 1 then sends the patient ID to the report storage apparatus 200 (Step S104).

An interpretation report of a previous examination with the patient ID added is searched in the report storage apparatus 200 (Step S105). In addition, in the report storage apparatus 200, image link information 212 of a key image embedded into the interpretation report of the previous examination is extracted (Step S106).

Alternatively, in the report storage apparatus 200, image ID of the key image embedded into the interpretation report of the previous examination is acquired (Step S106). The report storage apparatus 200 then sends the image link information 212 of the key image or the image ID of the key image to the medical image storage apparatus 100 (Step S107).

Medical image data (key image data) that corresponds to the image link information 212 is searched in the medical image storage apparatus 1 (Step S108). Alternatively, medical image data (key image data) with the image ID added is searched (Step S108). Subsequently, in the medical image storage apparatus 1, information regarding image-generating conditions included in the additional information added to the key image data is extracted (Step S109).

Image processing is then performed on the DICOM image data of the new examination in the medical image management apparatus 1 according to the image-generating conditions (Step S110). The newly generated DICOM image data is stored in the medical image management apparatus 1 (Step S111). When the newly generated DICOM image data is requested in the medical image observation apparatus 100, the medical image storage apparatus 1 then sends the requested DICOM image data to the medical image observation apparatus 1 (Step S112).

Next, the medical image storage apparatus 1, the medical image observation apparatus 100, and the report storage apparatus 200 will be described.

(Medical Image Storage Apparatus 1)

The medical image storage apparatus 1 will now be described. The medical image data with additional information added (DICOM image data) is sent by the medical image-imaging apparatus 400 to the medical image storage apparatus 1 via the network N after medical image data is generated by the medical image-imaging apparatus 400. For example, the tomographic image data with additional information added is sent to the medical image storage apparatus 1 after a plurality of sets of tomographic image data along an arbitrary direction in the subject is generated by the medical image-imaging apparatus 400.

A transmitter/receiver 2 of the medical image storage apparatus 1 receives the DICOM image data sent via the network N.

The transmitter/receiver 2 outputs the received DICOM image data to the image data-register 3. The transmitter/receiver 2 comprises, for example, a network adapter such as a LAN or a modem.

The transmitter/receiver 2 sends data to the medical image observation apparatus 100, the report storage apparatus 200, the report-creating apparatus 300, and the medical image-imaging apparatus 400 that are connected to the network N, or receives data from those apparatuses.

An image data-register 3 outputs the received DICOM image data to an image data storage 5 and registers the additional information of the DICOM image data in a database 4.

The database 4 stores the additional information added to the medical image data as being correlated with information regarding a storage position that specifies a storage destination of the DICOM image data to the image storage apparatus. For example, the database 4 stores the information regarding a patient's name, the patient ID, the examination ID, the series ID, the image ID, the information regarding imaging conditions, the information regarding image-generating conditions, the attribute information regarding an image, and the information regarding a storage position as being correlated with each other.

Moreover, when a plurality of sets of MPR image data is generated by an image-generating apparatus such as a 2D workstation or a 3D workstation, the plurality of sets of MPR image data is output to the image data-register 3 via the transmitter/receiver 2. The image data-register 3 outputs the plurality of sets of MPR image data to the image data storage 5 and registers the additional information added to each sets of the MPR image data in the database 4 as being correlated with the information regarding a storage position.

The image data storage 5 is provided with an image storage apparatus that comprises a plurality of HDDs (Hard Disk Drives) or NAS (Network Attached Storage). The image data storage 5 receives the DICOM image data from the image data-register 3 and stores it in a predetermined image storage apparatus. The image data storage 5 communicates with the database 4 and notifies the database 4 of the information regarding a storage position that shows the storage destination of the DICOM image data. The database 4 receives the information regarding a storage position from the image data storage 5 and stores the additional information as being correlated with the information regarding a storage position. Moreover, when the DICOM image data is deleted or modified, the image data storage 5 communicates with the database 4 and corrects the information regarding a storage position. Furthermore, the image data storage 5 corresponds to an example of the "medical image storage" of the present invention.

According to a request from a client terminal such as the medical image observation apparatus 100, an image data-searching part 6 reads from the image data storage 5 DICOM image data that corresponds to the request and outputs it to the transmitter/receiver 2.

The transmitter/receiver 2 sends the DICOM image data read by the image data-searching part 6 to the client terminal of the source of request.

A report searching condition-extracting part 9 receives the DICOM image data that belongs to an examination that has newly been conducted (new examination) and extracts patient ID included in the additional information of the DICOM image data. This patient ID is a retrieval key that is used when searching a report created for a previous examination. The transmitter/receiver 2 sends the patient ID to the report storage apparatus 200. Furthermore, as described above, the image data-register 3 outputs the DICOM image data of the new examination to the image data storage 5 and registers the additional information of the DICOM image data of the new examination in the database 4.

The report storage apparatus 200 searches an interpretation report with the patient ID added and sends image ID of a key image data or image link information (information regarding a storage position) of a key image embedded into the interpretation report to the medical image storage apparatus 1. This report storage apparatus 200 is described later.

The transmitter/receiver 2 receives the image ID or the image link information (information regarding a storage position) sent by the report storage apparatus. The transmitter/receiver 2 then outputs the image ID of the key image or the image link information (information regarding a storage position) of the key image to the image data-searching part 6.

When the image data-searching part 6 receives the image ID from the transmitter/receiver 2, it acquires from the database 4 information regarding a storage position of DICOM image data with the image ID added and reads the DICOM image data stored in the location that the information regarding a storage position shows from the image data storage 5. The image data-searching part 6 then outputs the read DICOM image data (key image data) to an image-generating condition-extracting part 7.

Moreover, when the image data-searching part 6 receives the image link information (information regarding a storage position) from the transmitter/receiver 2, it may read from the image data storage 5 the DICOM image data stored in the location that the image link information (information regarding a storage position) shows.

The image data-searching part 6 then outputs the read DICOM image data (key image data) to the image-generating condition-extracting part 7.

The image-generating condition-extracting part 7 extracts information regarding image-generating conditions of the key image data (hereinafter may be referred to as "information regarding image-generating conditions of the previous examination") from the additional information added to the key image data. As described above, information regarding image-generating conditions includes information regarding a cross-sectional position that shows a position of a cross-section, directional information that shows the direction of a medical image, thickness information that shows the thickness of a medical image, and information regarding image processing, etc. The image-generating condition-extracting part 7 then outputs the extracted information regarding image-generating conditions of the previous examination to the image-generator 8. In addition, the image-generating condition-extracting part 7 extracts information regarding imaging conditions (information regarding imaging conditions of the previous examination) from the additional information added to the key image data and outputs the information regarding imaging conditions of the previous examination to the image-generator 8.

Moreover, instead of the image-generating condition-extracting part 7 extracting the information regarding image-generating conditions and the information regarding imaging conditions, the image data-searching part 6 may acquire the information regarding image-generating conditions and the information regarding imaging conditions for the key image data that are managed in the database 4 and outputs them to the image-generator 8.

An image-generator 8 performs image processing on the DICOM image data that belongs to the new examination. This image processing follows the image-generating conditions that are indicated by the information regarding image-generating conditions of the previous examination extracted by the image-generating condition-extracting part 7. First, after the new DICOM image data (DICOM image data that belongs to the new examination) is received by the transmitter/receiver 2, the image data that belongs to the new examination is output to the image-generator 8. The image-generator 8 performs image processing on the DICOM image data that belongs to the new examination. This image processing follows the image-generating conditions shown by the information regarding image-generating conditions of the previous examination.

Specifically, the image-generator 8 performs image processing on the DICOM image data of the new examination according to the image-generating conditions of the key image data with the same patient ID as the patient ID added to the DICOM image data of the new examination.

For example, the image-generator 8 performs MPR processing on a plurality of sets of tomographic image data that belongs to the new examination according to conditions of a cross-sectional position, a direction, and a thickness that the information regarding image-generating conditions of the previous examination shows.

Thereby, MPR image data of the new examination is generated under the same image-generating conditions as the MPR image data of the previous examination. Furthermore, the image-generator 8 adds to the MPR image data of the new examination as additional information: information regarding a patient's name; patient ID; examination ID; series ID; image ID; information regarding imaging conditions; information regarding image-generating conditions; and attribute information regarding an image.

Moreover, the image-generator 8 may determine a cross-sectional position at which the key image data has been generated as the reference position and generate MPR image data of the new examination included within a predetermined range so that the reference position is centered. For example, the image-generator 8 may anteroposteriorly generate an arbitrary number of sets of MPR image data so that the reference position is centered. The number of MPR images and intervals between the MPR images are preliminarily set in the image-generator 8. Moreover, the operator may designate the number of images to be created and intervals of the images using a user interface, which is not shown in the figure. In addition, the operator may be able to change the thickness included in the image-generating conditions of the previous examination to an arbitrary thickness using the user interface.

Moreover, the image-generator 8 acquires the information regarding imaging conditions of the previous examination from the image-generating condition-extracting part 7 and compares the site of the patient who had undergone imaging in the new examination with the site of the patient who had undergone imaging in the previous examination in order to determine whether the imaged sites are the same. To be more precise, the image-generator 8 compares the site shown by the information regarding an imaging site (information regarding imaging site of the new examination) added to the DICOM image data of the new examination, with the site shown by the information regarding an imaging site included in the information regarding imaging conditions of the previous examination in order to determine whether the imaged sites are the same.

Subsequently, when the imaged site of the new examination and the imaged site of the previous examination are the same, the image-generator 8 performs image processing on the DICOM image data of the new examination. This is because when the imaged sites are the same, comparative interpretation is possible. For example, when the imaged site of the previous examination is a chest area and the imaged site of the new examination is a chest area, the imaged sites are the same and thus the image-generator 8 performs image processing on the DICOM image data of the new examination.

On the other hand, when the imaged site of the new examination and the imaged site of the previous examination are different, the image-generator 8 does not perform image processing on the DICOM image data of the new examination. This is because when the sites are different, they cannot be used for comparative interpretation. For example, the imaged site of the previous examination is a chest area and the imaged site of the new examination is an abdominal area, the imaged sites are different and thus the image-generator 8 does not perform image processing on the DICOM image data of the new examination.

The image-generator 8 then outputs the generated MPR image data of the new examination to the image data-register 3. The image data-register 3 outputs the MPR image data of the new examination to the image data storage 5 and registers the additional information of the MPR image data in the database 4.

Moreover, the image-generator 8 creates a list of an MPR image of the new examination and outputs it to the image data storage 5. The image data storage 5 stores the list. Subsequently, the medical image storage apparatus 1 sends the list to the medical image observation apparatus 100 after a request for acquiring a medical image is received from the medical image observation apparatus 100.

Thereby, the list is displayed in the medical image storage apparatus 100 and it is recognized that the MPR image of the new examination has already been generated and stored in the medical image storage apparatus 1.

Furthermore, the image data-register 3, the image data-searching part 6, the image-generating condition-extracting part 7, the image-generator 8, and the report searching condition-extracting part 9 are each provided with CPUs (Central Processing Units) and storage apparatuses such as ROM (Read Only Memory), RAM (Random Access Memory), and a HDD (Hard Disk Drive), which are not shown in the figure. An image data-registering program for executing the function of the image data-register 3, an image data-searching program for executing the function of the image data-searching part 6, an image-generating conditions-extracting program for executing the function of the image-generating condition-extracting part 7, and image-generating program for executing the function of the image-generator 8, and a report searching condition-extracting program for executing the function of the report searching condition-extracting part 9 are all stored in the storage apparatus. The function of each part is then executed by the CPU executing each of the programs stored in the storage apparatus.

Furthermore, in the present embodiment, the image data-searching part 6 corresponds to an example of the "medical image data-reading part" of the present invention.

(Report Storage Apparatus 200)

Next, the report storage apparatus 200 will be described. The report storage apparatus 200 is provided with a transmitter/receiver 201, a report storage 202, a report-searching part 203, and a key image-searching part 204.

The report storage 202 stores an interpretation report. For example, the report storage 202, as shown in FIG. 2, stores the report 210 that includes the image link information 211 (information regarding a storage position) and the retrieval information 212.

Furthermore, the retrieval information 212, as described above, includes information such as information regarding the examination date and time, information regarding a patient's name, patient ID, examination ID, and image ID.

The transmitter/receiver 201 receives a request for searching an interpretation report sent by the medical image storage apparatus 1. For example, the transmitter/receiver 201 receives patient ID sent by the medical image storage apparatus 1 and outputs the patient ID to the report-searching part 203. The transmitter/receiver 201, for example, comprises a network adapter such as a LAN or a modem.

The report-searching part 203 searches in the report storage 202 in order to read the interpretation report. The report-searching part 203 acquires a retrieval key sent by the medical image storage apparatus 1 and reads from the report storage 202 an interpretation report including retrieval information 212 that corresponds to this retrieval key. For example, if patient ID is sent by the medical image storage apparatus 1 as a retrieval key, the report-searching part 203 reads an interpretation report including retrieval information 212 that corresponds to the patient ID from the report storage 202. The report-searching part 203 then outputs the read interpretation report to the key image-searching part 204. Furthermore, the report-searching part 203 reads the latest interpretation report among the interpretation reports of the previous examinations. Moreover, the report-searching part 203 may receive a designation such as an imaged site and date and time and read an interpretation report that corresponds to the designated condition.

The key image-searching part 204 receives the interpretation report read by the report-searching part 203 and acquires image ID of a key image or image link information 211 (information regarding a storage position) of a key image embedded into the interpretation report. The key image-searching part 204 then outputs the image ID of the key image or the image link information 211 (information regarding a storage position) of the key image to the transmitter/receiver 201.

The transmitter/receiver 201 sends the image ID of the key image or the image link information 211 (information regarding a storage position) of the key image acquired by the key image-searching part 204 to the medical image storage apparatus 1.

Furthermore, the report-searching part 203 may read a previous interpretation report from the report storage 202 and further read a previous interpretation report to which the interpretation report is referring from the report storage 202. For example, if information regarding a storage position, etc., in another interpretation report is embedded into a previous interpretation report, the report-searching part 203 reads the referenced previous interpretation report from the report storage 202 based on the information regarding the storage position. In this case, the key image-searching part 204 acquires image link information (information regarding a storage position) of a key image or image ID of a key image embedded into the referred previous interpretation report. The transmitter/receiver 201 then outputs the image link information (information regarding a storage position) or the image ID of the key image to the medical image storage apparatus 1.

Furthermore, the report-searching part 203 and the key image-searching part 204 are each provided with CPUs and storage apparatuses such as ROM, RAM, and a HDD, which are not shown in the figure. A report-searching program for executing the function of the report-searching part 203 and a key image-searching program for executing the function of the key image-searching part 204 are stored in the storage apparatus. The CPU executing each of the programs stored in the storage apparatus then executes the function of each part.

Furthermore, in the present embodiment, the report-searching part 203 and the key image-searching part 204 comprise an example of the "medical image data-specifying part" of the present invention.

(Medical Image Observation Apparatus 100)

Next, the medical image observation apparatus 100 will be described. The medical image observation apparatus 100 is provided with a user interface 101, a transmitter/receiver 102, a controller 103, a storage 104, and an image-generator 105.

The user interface (UI) 101 is provided with a displaying part and an operating part. The displaying part comprises a monitor such as a CRT or a liquid crystal display and displays a medical image.

The operating part comprises an input apparatus such as a mouse and a keyboard and receives input from an operator. To acquire DICOM image data of a desired patient from the medical image storage apparatus 1, an operator enters patient ID that specifies the desired patient using the user interface. Moreover, DICOM image data included in a specific examination or DICOM image data included in a specific series may be acquired by entering examination ID and series ID in addition to the patient ID.

The transmitter/receiver 102 receives patient ID from the user interface 101 and sends the patient ID to the medical image storage apparatus 1. The transmitter/receiver 102 then receives DICOM image data sent by the medical image storage apparatus 1. The transmitter/receiver 102 comprises, for example, a network adapter such as a LAN or a modem and sends data to the medical image storage apparatus 1 connected to the network N or receives data from the medical image observation apparatus 1.

The controller 103 is connected to each part of the medical image observation apparatus 100 and controls the processes of each part. For example, the controller 103 stores, in the storage 104, DICOM image data that the transmitter/receiver 102 has received from the medical image storage apparatus 1. Moreover, the controller 103 reads DICOM image data from the storage 104 and displays medical images based on the DICOM image data on the displaying part of the user interface 101. For example, the controller 103 displays MPR images (based on MPR image data of a previous examination) next to MPR images (based on MPR image data of a new examination) on the displaying part of the user interface 101.

Furthermore, the controller 103 is provided with a CPU and a storage apparatus such as ROM, RAM, and a HDD, which are not shown in the figure. The storage apparatus stores a controlling program. The processes of each part of the medical image observation apparatus 100 are controlled by the CPU executing the controlling program.

The image-generator 105 reads DICOM image data from the storage 104 and performs image processing (e.g. MPR processing or volume rendering) on the DICOM image data in order to generate medical image data (e.g. MPR image data and 3-dimensional image data). The controller 103 stores the medical image data generated by the image-generator 105 in the storage 104. Furthermore, in the first embodiment, the image-generator 105 may not be provided in the medical image observation apparatus 100.

The image-generator 105 is provided with a CPU and a storage apparatus such as ROM, RAM, and a HDD, which are not shown in the figure. An image-generating program for executing the function of the image-generator 104 is stored in the storage apparatus.

The CPU executes the image-generating program in order to perform image processing such as MPR processing on the DICOM image data.

(Processes)

Figure 4:
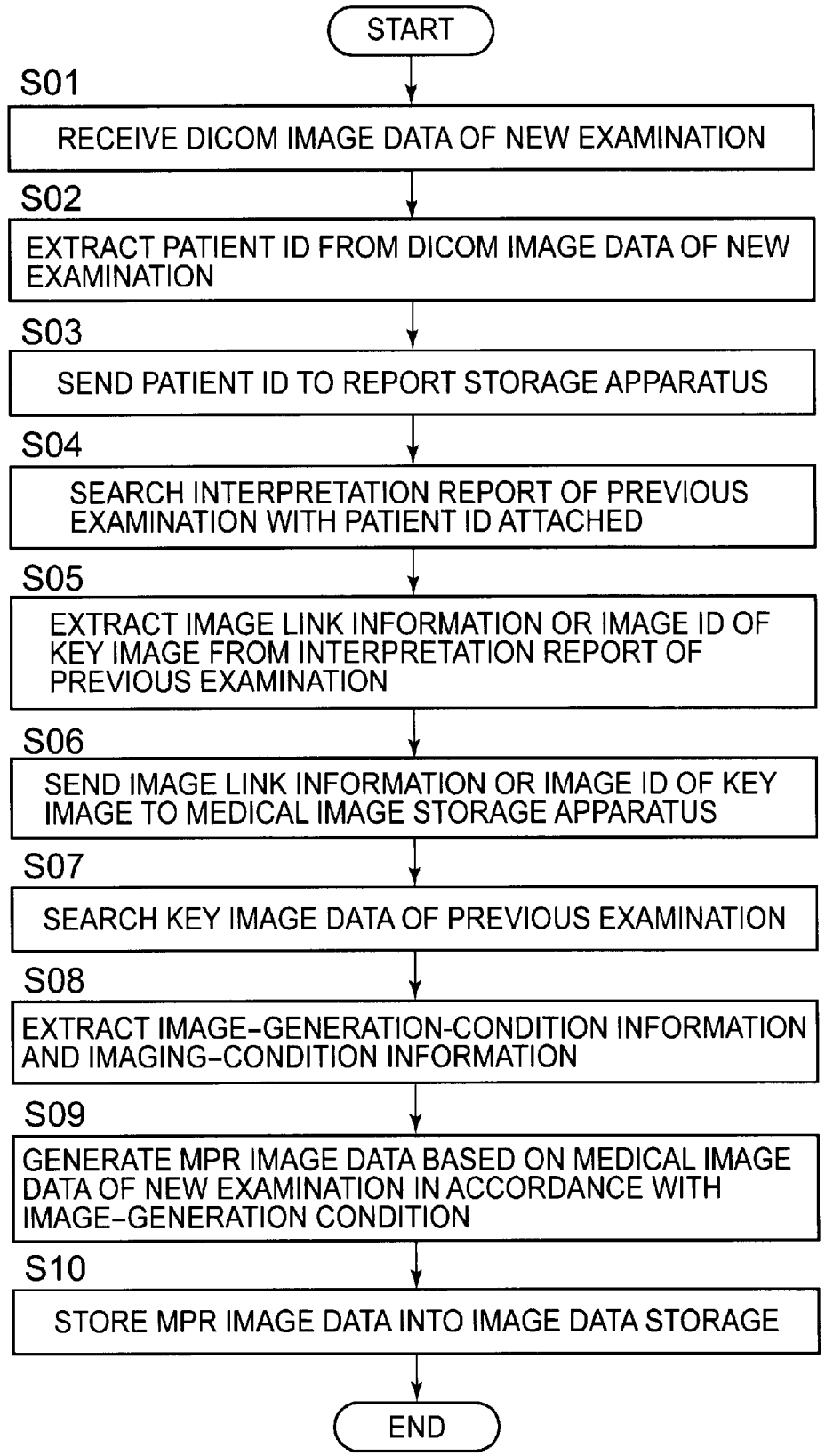
FIG. 4 is a flow chart illustrating a sequence of processes of the medical image observation system according to the first embodiment of the present invention.

Next, a sequence of processes of the medical image observation system according to the first embodiment is described with reference to FIG. 4. FIG. 4 is a flow chart illustrating a sequence of processes of the medical image observation system according to the first embodiment of the present invention.

(Step S01)

Firstly, DICOM image data of a new examination is generated by performing imaging in the medical image-imaging apparatus 400.

For example, the medical image-imaging apparatus 400 acquires a plurality of sets of tomographic image data along an arbitrary direction in a subject. The medical image-imaging apparatus 400 sends the DICOM image data (tomographic image data) of the new examination to the medical image storage apparatus 1. The transmitter/receiver 2 of the medical image storage apparatus 1 receives the DICOM image data of the new examination from the medical image-imaging apparatus 400 and outputs it to the image data-register 3. The image data-register 3 outputs the DICOM image data of the new examination to the image data storage 5 and further registers the additional information in the database 4 as being correlated with the information regarding a storage position.

(Step S02)

The report searching condition-extracting part 9 extracts patient ID added to the DICOM image data of the new examination as the additional information. This patient ID is used as a retrieval key when searching an interpretation report of a previous examination in the report storage apparatus 200.

(Step S03)

The transmitter/receiver 2 of the medical image storage apparatus 1 sends, to the report storage apparatus 200, the patient ID that was extracted in the report-searching condition-extracting part 9.

(Step S04)

The transmitter/receiver 201 of the report storage apparatus 200 receives the patient ID from the medical image storage apparatus 1 and outputs the patient ID to the report-searching part 203. The report-searching part 203 acquires from the report storage 202 an interpretation report that has retrieval information that matches the patient ID and outputs the interpretation report to the key image-searching part 204. This interpretation report corresponds to the interpretation report of the previous examination.

(Step S05)

The key image-searching part 204 extracts image link information (information regarding a storage position) of a key image embedded into the interpretation report of the previous examination.

Alternatively, the key image-searching part 204 extracts the image ID of the key image embedded into the interpretation report of the previous examination.

(Step S06)

transmitter/receiver 201 sends the image link information (information regarding a storage position) of the key image to the medical image storage apparatus 1. Alternatively, the transmitter/receiver 201 sends the image ID of the key image to the medical image storage apparatus 1.

(Step S07)

The transmitter/receiver 2 of the medical image storage apparatus 1 receives the image link information (information regarding a storage position) or the image ID sent by the report storage apparatus 200 and outputs it to the image data-searching part 6. The image data-searching part 6 reads medical image data (key image data) stored in a location that the image link information (information regarding a storage position) of the key image shows from the image data storage 5. Alternatively, the image data-searching part 6 acquires information regarding a storage position that corresponds to the image ID from the database and reads medical image data (key image data) stored in a location that the information regarding a storage position shows from the image data storage 5. The image data-searching part 6 then outputs the read medical image data (key image data) to the image-generating condition-extracting part 7.

(Step S08)

The image-generating condition-extracting part 7 extracts information regarding image-generating conditions and information regarding imaging conditions of the previous examination included in the additional information of the key image data and outputs the information regarding image-generating conditions and the information regarding imaging conditions of the previous examination to the image-generator 8.

(Step S09)

The image-generator 8 receives the DICOM image data (tomographic image data) of the new examination from the transmitter/receiver 2 and compares a site that the information regarding imaging site added to the tomographic image data of the new examination shows with a site that the information regarding imaging site included in the information regarding imaging conditions of the previous examination shows in order to determine whether the sites are the same. When the imaged sites are the same, the image-generator 8 performs image processing on the plurality of sets of tomographic image data of the new examination according to image-generating conditions that the information regarding image-generating conditions of the previous examination shows. For example, the image-generator 8 performs MPR processing on the plurality of sets of tomographic image data of the new examination according to the conditions of a cross-sectional position, a direction, and a thickness that the information regarding image-generating conditions of the previous examination shows. Thereby, MPR image data of the new examination is generated under the same image-generating conditions as the MPR image data of the previous examination. In addition, the image-generator 8 may determine a cross-sectional position at which the key image data has been generated as the reference position and anteroposteriorly generate an arbitrary number of sets of MPR image data around the reference position. The image-generator 8 then outputs the generated MPR image data of the new examination to the image data-register 3.

(Step S10)

The image data-register 3 outputs the MPR image data generated in the image-generator 8 to the image data storage 5 and registers the additional information of the MPR image data in the database 4 as being correlated with the information regarding a storage position.

Subsequently, when the operator enters the image ID of the MPR image of the new examination in the medical image observation apparatus 100 using the user interface 101, the transmitter/receiver 102 sends the image ID to the medical image storage apparatus 1. The image data-searching part 6 reads MPR image data that corresponds to the image ID from the image data storage 5 and the transmitter/receiver 2 sends the MPR image data to the medical image observation apparatus 100. The controller 103 receives the MPR image data via the transmitter/receiver 102 and causes the displaying part of the use interface 101 to display an MPR image based on the MPR image data.

For example, the image-generator 8 creates a list of the MPR image of the new examination and outputs it to the image data storage 5. The image data storage 5 stores the list. Subsequently, when a request for acquiring a medical image is received from the medical image observation apparatus 100, the medical image storage apparatus 1 sends the list to the medical image observation apparatus 100. The controller 103 of the medical image observation apparatus 100 causes the displaying part of the use interface 101 to display the list of the MPR image of the new examination as a reference list.

Thereby, the operator recognizes in the medical image observation apparatus 100 that the MPR image of the new examination has already been generated and stored in the medical image storage apparatus 1.

Subsequently, when the operator designates a desired MPR image in the list using the user interface 101, the transmitter/receiver 102 sends the image ID of the MPR image to the medical image storage apparatus 1. The image data-searching part 6 of the medical image storage apparatus 1 reads MPR image data with the image ID added from the image data storage 5 and the transmitter/receiver 2 sends the MPR image data to the medical image observation apparatus 100. The controller 103 of the medical image observation apparatus 100 causes the displaying part of the user interface 101 to display an MPR image based on the MPR image data.

Moreover, to compare and interpret the MPR image of the previous examination and the MPR image of the new examination, the operator enters the image ID of the MPR image of the previous examination and the image ID of the MPR image of the new examination using the user interface 101. The medical image storage apparatus 1 sends the MPR image data of the previous examination and the MPR image data of the new examination that correspond to the image ID to the medical image observation apparatus 100. The controller 103 of the medical image observation apparatus 100 causes the displaying part of the user interface 101 to display the MPR image of the previous examination next to the MPR image of the new examination.

As stated above, by preliminarily generating a medical image that is possible to be referred in comparative interpretation in the medical image storage apparatus 1, the preliminarily generated medical image can only be sent to the medical image observation apparatus 100 in comparative interpretation. Thereby, a plurality of sets of medical image data to generate the medical image that is referred in comparative interpretation does not need to be sent to the medical image observation apparatus 100. Therefore, a volume of medical image data to be sent can be minimized, allowing reducing the time required to send the medical image data. Specifically, because it becomes possible to send only the medical image data of the new examination necessary for comparative interpretation to the medical image observation apparatus 100, it is possible to reduce the amount of time required for transmission, thereby enabling more efficient interpretation, etc. Moreover, large-capacity memory does not need to be provided in the medical image observation apparatus 100.

For example, because the MPR image of the new examination that corresponds to the key image may be used for comparative interpretation, the MPR image data of the new examination is created preliminarily. Thereby, it is possible to send only the MPR image data of the new examination necessary for comparative interpretation to the medical image observation apparatus 100. Consequently, it is possible to reduce the amount of time required to transmit the image data, thereby enabling more efficient interpretation, etc. Specifically, in comparative interpretation, it is possible to read the MPR image data of the new examination in the medical image observation apparatus 100 and quickly display the MPR image of the previous examination and the MPR image of the new examination.

Moreover, the amount of work is advantageously eliminated because it is unnecessary to generate medical image data for comparative interpretation in the medical image observation apparatus 100. Thereby, it is possible to reduce the burden of the operator. For example, because it is unnecessary to designate a desired cross-section in order to generate MPR image data, the work is eliminated reducing the burden of the operator.

Furthermore, in the report storage apparatus 200, the key image-searching part 204 may acquire the image ID of all key images or image link information (information regarding a storage position) of all key images from a previous interpretation report when a plurality of sets of key image data is embedded into the previous interpretation report. The key image-searching part 204 then outputs the image ID of all of the key images or the image link information (information regarding a storage position) of all of the key images to the transmitter/receiver 201. The transmitter/receiver 201 sends the image ID of all of the key images or the image link information (information regarding a storage position) of all of the key images to the medical image storage apparatus 1. The image data-searching part 6 of the medical image storage apparatus 1 reads all key image data from the image data storage 5 based on the image link information (information regarding a storage position) of each of the key images or the image ID of each of the key images. The image-generating condition-extracting part 7 extracts image-generating conditions and information regarding an imaging site of the previous examination from all of the key image data. The image-generator 8 may then generate MPR image data of the new examination by performing image processing on the DICOM image data of the new examination according to each of the image-generating conditions.

Moreover, the medical image storage apparatus 1 may send the remaining medical image data of the new examination to the medical image observation apparatus 100 as well as the medical image data of the new examination sent to the medical image observation apparatus 100. For example, when there is a request from the medical image observation apparatus 100 (client) for transmission to the medical image storage apparatus 1, the transmitter/receiver 2 of the medical image storage apparatus 1 sends the remaining medical image data of the new examination to the medical image observation apparatus 100.

Moreover, when the communication speed of the network N is slow, the remaining medical image data of the new examination may be sent to the medical image observation apparatus 100 later.

Moreover, when the capacity of the storage 104 of the medical image observation apparatus 100 is limited, the controller 103 of the medical image observation apparatus 100 may move the medical image data stored in the storage 104 to another storage apparatus and subsequently send the remaining medical image data to the medical image storage apparatus 1 via the transmitter/receiver 102. The image data-searching part 6 of the medical image storage apparatus 1 receives the request and reads the remaining medical image data of the new examination from the image data storage 5 and the transmitter/receiver 2 sends the remaining medical image data to the medical image observation apparatus 100.

Second Embodiment

Figure 5:
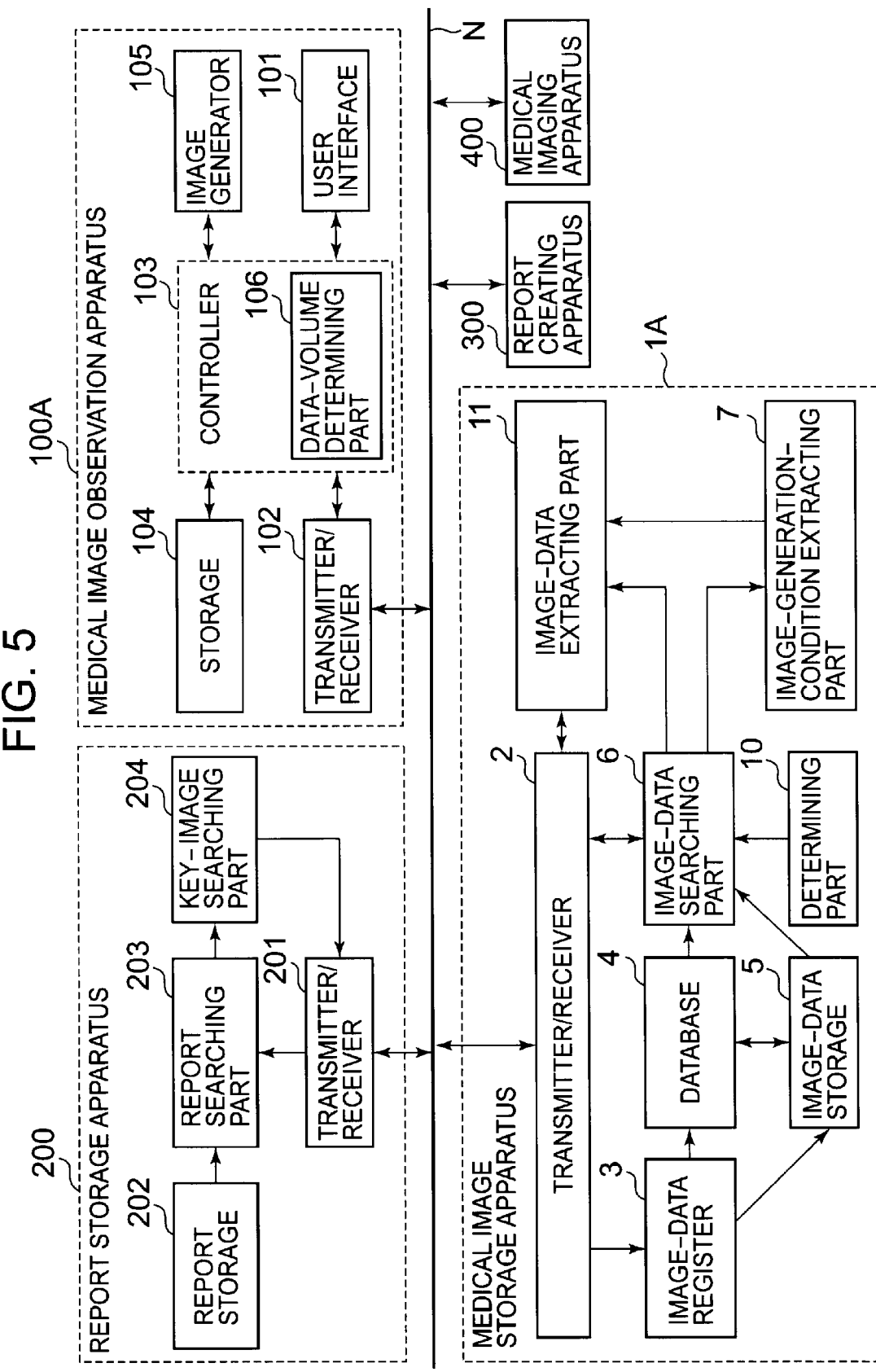
FIG. 5 is a block diagram illustrating a medical image observation system according to the second embodiment of the present invention.

Next, a medical image observation system according to a second embodiment of the present invention is described with reference to FIG. 5. FIG. 5 is a block diagram illustrating the medical image observation system according to the second embodiment of the present invention.

As shown in FIG. 5, in an in-hospital system according to the second embodiment, a medical image storage apparatus (medical image server) 1A, a medical image observation apparatus (client terminal) 100A, a report storage apparatus (report server) 200, a report-creating apparatus 300, and a medical image-imaging apparatus 400 are connected to each other via the network N.

In the second embodiment, the medical image storage apparatus 1A, the medical image observation apparatus 100A, and the report storage apparatus 200 comprise an example of the medical image observation system of the present invention. The medical image observation system according to the second embodiment is provided with medical image storage apparatus 1A instead of the medical image storage apparatus 1 and with the medical image observation apparatus 100A instead of the medical image observation apparatus 100. Here, the medical image storage apparatus 1A and the medical image observation apparatus 100A will be described. The descriptions of the report storage apparatus 200 and the medical image diagnosis apparatus 400 have been omitted, as the report storage apparatus 200 and the medical image diagnosis apparatus 400 correlate to the abovementioned first embodiment. Furthermore, the in-hospital system according to the second embodiment may be provided with an image-generating apparatus such as a 2D workstation or a 3D workstation similarly to the first embodiment. In this second embodiment, as an example, a case is described in which the medical image-imaging apparatus 400 acquires a plurality of sets of tomographic image data along an arbitrary direction in a subject (Outline of Processes)

Figure 6:
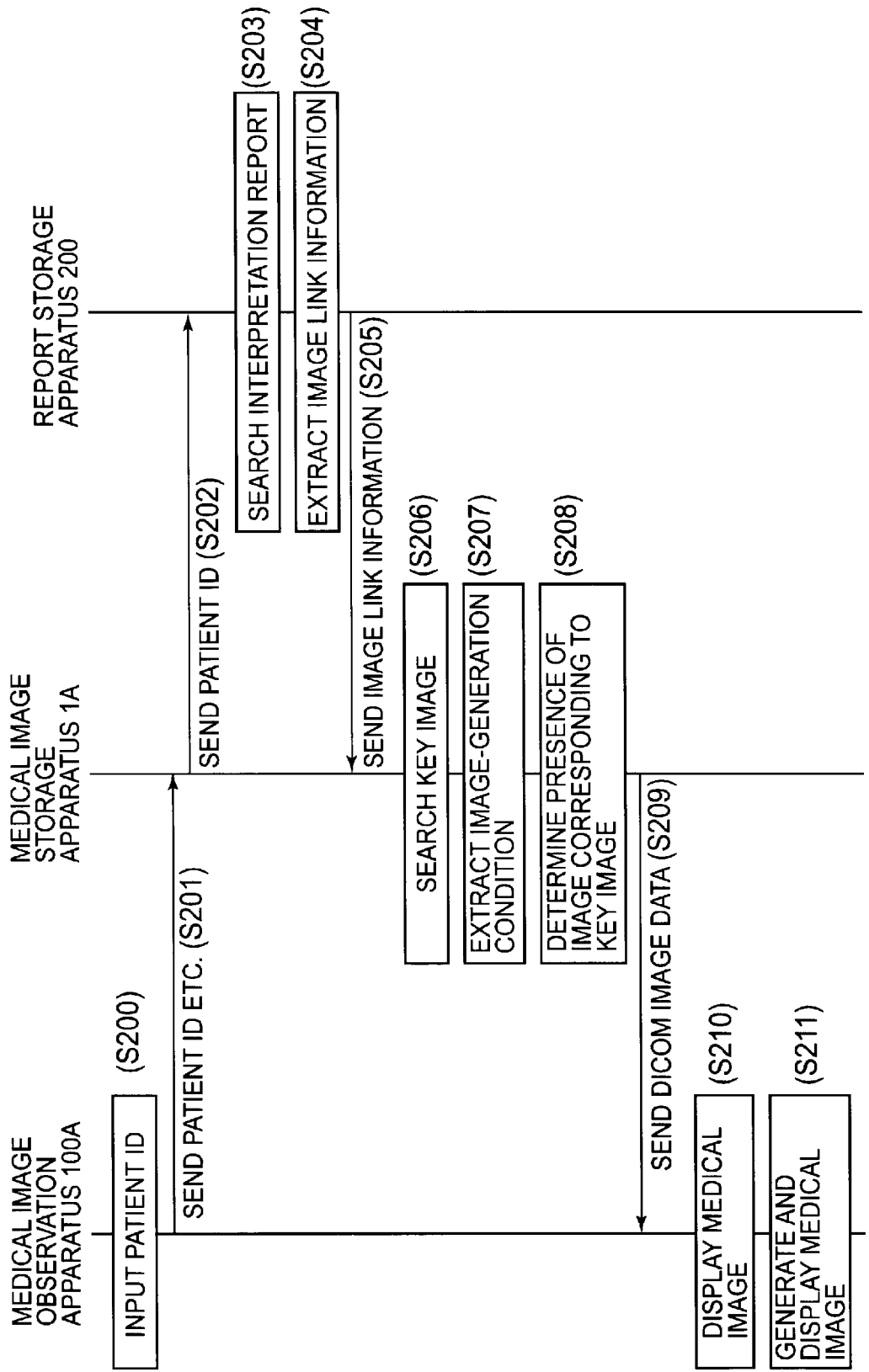
FIG. 6 is a sequence diagram illustrating the outline of processes of the medical image observation system according to the second embodiment of the present invention.

Here, the outline of processes of the medical image observation system according to the second embodiment is described with reference to FIG. 6. FIG. 6 is a sequence diagram illustrating the outline of processes of the medical image observation system according to the second embodiment of the present invention.

Firstly, an operator designates patient ID of a desired patient in the medical image observation apparatus 100A (Step S200). The medical image observation apparatus 100A sends the patient ID to the medical image storage apparatus 1A (Step S201). At this time, the medical image storage apparatus 1A sends information that shows a readable volume of data to the medical image storage apparatus 1A (Step S201).

The medical image storage apparatus 1A receives the patient ID and the information regarding the readable volume of data from the medical image observation apparatus 1A and sends the patient ID to the report storage apparatus 200 (Step S202). In the report storage apparatus 200, an interpretation report of a previous examination with the patient ID added is searched (Step S203). In addition, in the report storage apparatus 200, image link information 212 of a key image embedded into the interpretation report of the previous examination is extracted (Step S204). Alternatively, in the report storage apparatus 200, image ID of the key image embedded into the interpretation report of the previous examination is acquired (Step S204). The report storage apparatus 200 then sends the image link information 212 of the key image or the image ID of the key image to the medical image storage apparatus 1A (Step S205).

In the medical image storage apparatus 1A, DICOM image data (key image data) that corresponds to the image link information 212 is searched (Step S206). Alternatively, DICOM image data (key image data) with the image ID added is searched (Step S206).

Subsequently, in the medical image storage apparatus 1A, information regarding image-generating conditions included in the additional information added to the key image data is extracted (Step S207). In the medical image storage apparatus 1A, it is then determined whether the DICOM image data of the new examination includes DICOM image data that corresponds to the key image data of the previous examination (Step S208). When the DICOM image data of the new examination includes DICOM image data that corresponds to the key image data, the medical image storage apparatus 1A sends the corresponding DICOM image data to the medical image observation apparatus 100A (Step S209). On the other hand, when the DICOM image data of the new examination does not include DICOM image data that corresponds to the key image data, the medical image storage apparatus 1A sends DICOM image data to generate the DICOM image data that corresponds to the key image data to the medical image observation apparatus 100A (Step S209).

At this time, the medical image storage apparatus 1A sends the DICOM image data that corresponds to the readable volume of data to the medical image observation apparatus 100A.

When the medical image observation apparatus 100A receives DICOM image data that corresponds to the key image data of the previous examination, it displays a medical image on the displaying part (Step S210). On the other hand, when the medical image observation apparatus 100A receives DICOM image data that does not correspond to the key image data, it generates DICOM image data that corresponds to the key image data based on the DICOM image data and displays a medical image (Step S211).

Next, the medical image observation apparatus 100A and the medical image storage apparatus 1A will be described.

(Medical Image Observation Apparatus 100A)

First, the medical image observation apparatus 100A will be described. The medical image observation apparatus 100A is provided with a user interface 101, a transmitter/receiver 102, a controller 103, a storage 104, an image-generator 105, and a data-volume determining part 106.

The user interface 101, transmitter/receiver 102, controller 103, storage 104, and image-generator 105 have the same functions as the abovementioned first embodiment.

In the second embodiment, an operator enters the patient ID of a desired patient using the user interface 101. In addition, the operator designates to read DICOM image data using the user interface 101. For example, the operator enters the patient ID of a patient for examination using the user interface 101 and further designates to read DICOM image data included in a new examination.

The transmitter/receiver 102 sends the patient ID and the instruction for reading the DICOM image data to the medical image storage apparatus 1A.

Based on the free space of the storage 104 and the communication speed of the transmitter/receiver 102, the data-volume determining part 106 determines a volume of data of the DICOM image data that the medical image observation apparatus 100A reads. For example, the free space of the storage 104, the communication speed of the network, and the upper limit of the readable volume of data are correlated with each other in a table, which is preliminarily stored in a storage, which is not shown in the figure. The data-volume determining part 106 determines the upper limit of the readable volume of data by referring the table stored in the storage. Here, the volume of data of the DICOM image data that the medical image observation apparatus 100A reads is described with reference to FIG. 7. FIG. 7 is a table illustrating the volume of data of the image data that the medical image observation apparatus reads.

For example, if the free space (amount of memory) of the storage 104 is 512 MB or less and the speed of the communication path is 10 Mbps or less, the data-volume determining part 106 determines a volume of data of 100 CT images as the upper limit of the readable volume of data, for example, by converting into CT images. Moreover, if the free space (amount of memory) of the storage 104 is 1 GB or more and the speed of the communication path is 1 Gbps or more, the data-volume determining part 106 determines a volume of data of 1600 images as the upper limit of the readable volume of data. The transmitter/receiver 2 then sends information that shows the volume of data determined by the data-volume determining part 106 to the medical image storage apparatus 1A.

It should be noted that, in the example shown in FIG. 7, the number of images is converted into the number of CT images, but it may be converted, for example, into other medical images such as MRI images. Moreover, it may be converted into a data capacity of a file.

(Medical Image Storage Apparatus 1A)

Next, the medical image storage apparatus 1A will be described. The medical image storage apparatus 1A is provided with a transmitter/receiver 2, an image data-register 3, a database 4, an image data storage 5, an image data-searching part 6, an image-generating condition-extracting part 7, a determining part 10, and an image data-extracting part 11.

The transmitter/receiver 2, image data-register 3, database 4, image data storage 5, image data-searching part 6, and image-generating condition-extracting part 7 have the same functions as those of the abovementioned first embodiment.

Similarly to the abovementioned first embodiment, the image data-register 3 outputs DICOM image data to the image data storage 5 and resisters additional information of the DICOM image data in the database 4. The database 4 stores the additional information as being correlated with information regarding a storage position of the medical image data. The image data storage 5 receives the DICOM image data from the image data-register 3 and causes a predetermined image storage apparatus to store it.

The transmitter/receiver 2 receives patient ID and an instruction for reading the DICOM image data sent by the medical image observation apparatus 100A. The transmitter/receiver 2 then sends the patient ID to the report storage apparatus 200. In addition, the transmitter/receiver 2 receives information that shows the readable volume of data sent by the medical image observation apparatus 100A and outputs it to the image data-searching part 6 and the image data-extracting part 11.

The report storage apparatus 200, similarly to the abovementioned first embodiment, searches an interpretation report with the patient ID added and sends image ID of key image data or image link information (information regarding a storage position) of a key image embedded into the interpretation report to the medical image storage apparatus 1A. This report storage apparatus 200 correlates to the first embodiment, so a description thereof has been omitted.

The transmitter/receiver 2 receives the image ID or the image link information (information regarding a storage position) sent by the report storage apparatus 200. The transmitter/receiver 2 then outputs the image ID of the key image or the image link information (information regarding a storage position) of the key image to the image data-searching part 6.

When the image data-searching part 6 receives the image ID of the key image data from the transmitter/receiver 2, it acquires from the database 4 information regarding a storage position of DICOM image data with the image ID added and reads DICOM image data stores in a location that the information regarding a storage position shows from the image data storage 5. The image data-searching part 6 then outputs the read DICOM image data (key image data) to the image-generating condition-extracting part 7.

Moreover, when the image data-searching part 6 receives the image link information (information regarding a storage position) from the transmitter/receiver 2, it may read from the image data storage 5 DICOM image data stored in a location that the image link information (information regarding a storage position) shows. The image data-searching part 6 then outputs the read DICOM image data (key image data) to the image-generating condition-extracting part 7.

The image-generating condition-extracting part 7 extracts information regarding image-generating conditions (information regarding image-generating conditions of the previous examination) from the additional information added to the key image data.

Similarly to the abovementioned first embodiment, the information regarding image-generating conditions includes information (e.g. information regarding cross-sectional position that shows a position of a cross-section; directional information that shows a direction of a medical image; thickness information that shows a thickness of a medical image; and information regarding image processing). The image-generating condition-extracting part 7 then outputs the extracted information regarding image-generating conditions of the previous examination to the image data-searching part 6, the determining part 10, and the image data-extracting part 11.

In addition, the image-generating condition-extracting part 7 extracts information regarding imaging conditions from the additional information added to the key image data and outputs the information regarding imaging conditions of the previous examination to the determining part 10.

Moreover, when the DICOM image data of the new examination is received by the transmitter/receiver 2, the DICOM image data of the new examination is output to the image-generating condition-extracting part 7. The image-generating condition-extracting part 7 extracts information regarding image-generating conditions (information regarding image-generating conditions of the new examination) from the additional information added to the DICOM image data of the new examination. In addition, the image-generating condition-extracting part 7 extracts information regarding imaging conditions (information regarding imaging conditions of the new examination) from the additional information added to the DICOM image data of the new examination. The image-generating condition-extracting part 7 then outputs the extracted information regarding image-generating conditions and the extracted information regarding imaging conditions of the new examination to the determining part 10.

Moreover, instead of the image-generating condition-extracting part 7 extracting the information regarding image-generating conditions and the information regarding imaging conditions, the image data-searching part 6 may extract the information regarding image-generating conditions and the information regarding imaging conditions from the key image data managed in the database 4 and the DICOM image data of the new examination.

The determining part 10 determines whether DICOM image data that corresponds to the DICOM image data (key image data) of the previous examination is available in the DICOM image data of the new examination. For example, the determining part 10 acquires information regarding the image-generating conditions of the previous examination and the information regarding image-generating conditions of the new examination from the image-generating condition-extracting part 7 and compares the cross-sectional positions and the directions, etc., that the information regarding image-generating conditions shows in order to determine whether DICOM image data of the new examination that corresponds to the key image data is available.

Here, tomographic image data will be described as an example. When directional information included in information regarding image-generating conditions shows a coronal direction, it indicates that the tomographic image is a coronal image captured from the coronal direction. Moreover, when directional information shows an axial direction, it indicates that the tomographic image is an axial image captured from the axial direction. Moreover, when directional information shows a sagittal direction, it indicates that the tomographic image is a sagittal image captured from the sagittal direction. Furthermore, the coronal direction, axial direction, and sagittal direction are directions that are perpendicular to each other, and the coronal image, axial image, and sagittal image are tomographic images that are perpendicular to each other.

For example, when directional information included in information regarding image-generating conditions of a previous examination shows an axial direction and directional information included in information regarding image-generating conditions of a new examination shows an axial direction, the directions are the same, so the determining part 10 determines that DICOM image data (tomographic image data) of the new examination that corresponds to the key image data is available. The determining part 10 then outputs the judgment results to the image data-searching part 6.

On the other hand, if directional information included in information regarding image-generating conditions of a previous examination shows a coronal direction and directional information included in information regarding image-generating conditions of a new examination shows an axial direction, the directions are not the same and thus the determining part 10 determines that DICOM image data (tomographic image data) of the new examination that corresponds to the key image data is not available. The determining part 10 then outputs the judgment results to the image data-searching part 6.

When the image data-searching part 6 receives the judgment results from the determining part 10, it reads the DICOM image data of the new examination from the image data storage 5 according to the judgment results.

(In Cases in which Tomographic Image Data of the New Examination that Corresponds to the Key Image Data of the Previous Examination is Available)

For example, when it has been determined that tomographic image data of the new examination that corresponds to the key image data of the previous examination is available, the image data-searching part 6 receives the information regarding image-generating conditions of the previous examination from the image-generating condition-extracting part 7 and reads the tomographic image data of the new examination generated at a cross-sectional position that corresponds to the cross-sectional position of the key image data from the image data storage 5. For example, the image data-searching part 6 reads the tomographic image data of the new examination generated at the same cross-sectional position as the cross-sectional position of the key image data from the image data storage 5. Moreover, when tomographic image data of the new examination generated at the same cross-sectional position as the cross-sectional position of the key image data is not available, the image data-searching part 6 reads the tomographic image data of the new examination generated at a cross-sectional position closest to the cross-sectional position of the key image data from the image data storage 5.

In addition, the image data-searching part 6 determines the cross-sectional position of the key image data as the reference position and reads tomographic image data of the new examination included in a predetermined range from the image data storage 5 around the reference position. For example, the image data-searching part 6 anteroposteriorly reads an arbitrary number of sets of tomographic image data of the new examination from the image data storage 5 around the reference position. At this time, the image data-searching part 6 reads the tomographic image data of the new examination from the image data storage 5 according to the information that shows the readable volume of data sent by the medical image observation apparatus 100A. Specifically, the image data-searching part 6 reads tomographic image data with the volume of data according to the capacity of the memory provided with the medical image observation apparatus 100A and the communication speed from the image data storage 5. For example, when the free space (amount of memory) of the storage 104 is 512 MB or less and the speed of the communication path is 10 Mbps or less, it is possible to read 100 images of a volume of data and thus the image data-searching part 6 reads that amount of tomographic image data of the new examination from the image data storage 5.

The image data-searching part 6 outputs the read tomographic image data of the new examination to the transmitter/receiver 2. The transmitter/receiver 3 sends the tomographic image data of the new examination to the medical image observation apparatus 100A.

(In a Case in which Tomographic Image Data of the New Examination that Corresponds to the Key Image Data of the Previous Examination is not Available)

Moreover, when it has been determined that tomographic image data of the new examination that corresponds to the key image data of the previous examination is not available, the image data-searching part 6 reads tomographic image data of the new examination from the image data storage 5 and outputs the tomographic image data of the new examination to the image data-extracting part 11.

The image data-extracting part 11 extracts image data for generation of tomographic image data that corresponds to the key image data of the previous examination from a plurality of sets of tomographic image data included in the new examination based on the cross-sectional position that the information regarding image-generating conditions of the previous examination shows.

Specifically, the image data-extracting part 11 specifies the cross-sectional position of the key image data among the plurality of sets of tomographic image data included in the new examination and extracts image data included in the anteroposterior range of the specified position.

Figure 8A:
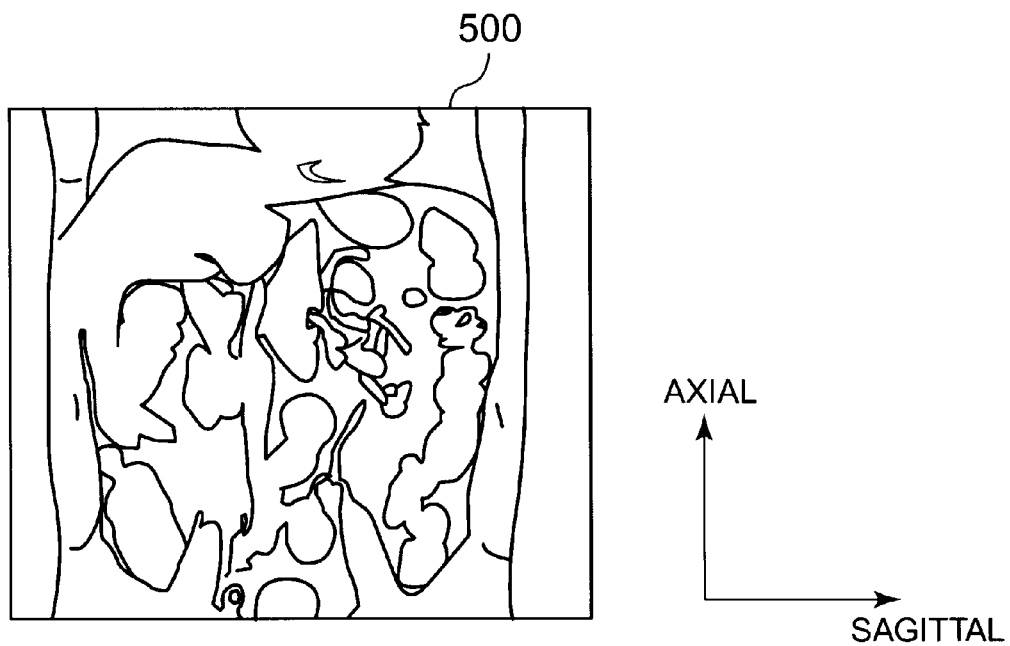
FIG. 8A is a diagram illustrating a key image of a previous examination.
Figure 8B:
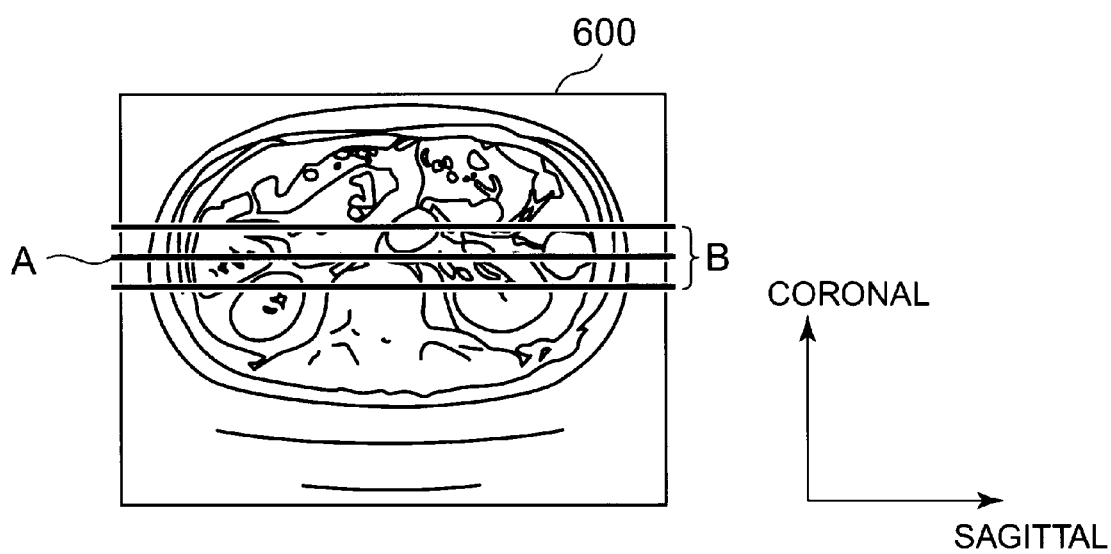
FIG. 8B is a diagram illustrating a medical image of a new examination.

Here, the range in which the image data is to be extracted from the tomographic image data of the new examination is described with reference to FIG. 8A, FIG. 8B, and FIG. 9. FIG. 8A is a diagram illustrating the key image of the previous examination. FIG. 8B is a diagram illustrating the medical image of the new examination. FIG. 9 is a diagram illustrating a frame format for describing the range in which image data is to be extracted from the medical image data of the new examination.

A key image 500 shown in FIG. 8A is a tomographic image acquired in the previous examination. In this example, the key image 500 is a coronal image captured from the coronal direction. On the other hand, a medical image 600 shown in FIG. 8B is a tomographic image acquired in the new examination. In this example, the medical image 600 is an axial image captured from the axial direction perpendicular to the coronal direction. As the above, because the imaging directions of the tomographic images are different between the previous examination and the new examination, tomographic image data that corresponds to the key image 500 of the previous examination is not available in the tomographic image data of the new examination.

Therefore, the image data-extracting part 11 specifies a position that corresponds to the cross-sectional position of the key image 500 (coronal image) of the previous examination in the medical image 600 (axial image) of the new examination. In the example shown in FIG. 8B, in the medical image 600 of the new examination, a position A is the position that corresponds to the cross-sectional position of the key image 500. The image data-extracting part 11 specifies the position A of the medical image 600 based on the cross-sectional position of the key image 500.

In addition, the image data-extracting part 11 specifies a range in which the image data is to be extracted based on the readable volume of data of the medical image observation apparatus 100A. For example, as shown in FIG. 8B, the image data-extracting part 11 determines the position A that corresponds to the cross-sectional position of the key image 500 (coronal image) as the reference position and determines a predetermined range B that extends in the coronal direction in the medical image 600 (axial image) as the range in which the image data is to be extracted.

Specifically, the image data-extracting part 11 specifies an extraction range in the coronal direction based on range B. The image data-extracting part 11 then extracts image data included in range B respectively from the plurality of sets of tomographic image data of the new examination and outputs it to the transmitter/receiver 2. At this time, the image data-extracting part 11 determines the size of range B based on the readable volume of data of the medical image observation apparatus 100A and extracts image data included in range B.

For example, as shown in FIG. 9, when a plurality of sets of tomographic image data (axial image data) is acquired along a predetermined direction (axial direction) in one series of the new examination, the series includes medical images 600A-600N (axial image). The image data-extracting part 11 extracts image data included in range B shown in diagonal line respectively from the medical images 600A-600N. The image data-extracting part 11 then outputs the image data included in range B to the transmitter/receiver 3. The transmitter/receiver 3 sends the image data included in range B to the medical image observation apparatus 100A.

The transmitter/receiver 102 of the medical image observation apparatus 100A receives the image data included in range B sent by the medical image storage apparatus 1A. The controller 103 causes the storage 4 to store the image data included in range B. The image-generator 105 then generates MPR image data of the cross-sectional position that corresponds to the cross-sectional position of the key image of the previous examination by performing MPR processing on the image data included in range B. For example, the medical image storage apparatus 1A sends the image-generating conditions of the key image of the previous examination to the medical image observation apparatus 100A. The image-generator 105 of the medical image observation apparatus 100A generates MPR image data of the new examination that corresponds to the key image of the previous examination by performing MPR processing on the image data included in range B according to the image-generating conditions of the previous examination. The controller 103 causes the displaying part of the user interface 101 to display an MPR image based on the MPR image data. In addition, the image-generator 105 may generate MPR image data in an arbitrary cross-section based on the image data included in range B.

In addition, similarly to the first embodiment, the controller 103 may cause the displaying part of the user interface 101 to display the MPR image of the previous examination next to the MPR image of the new examination. Thereby, the operator can compare and interpret the MPR images of the previous examination and the new examination.

(In a Case in which an Annotation is Added to the Key Image Data)

Figure 10A:
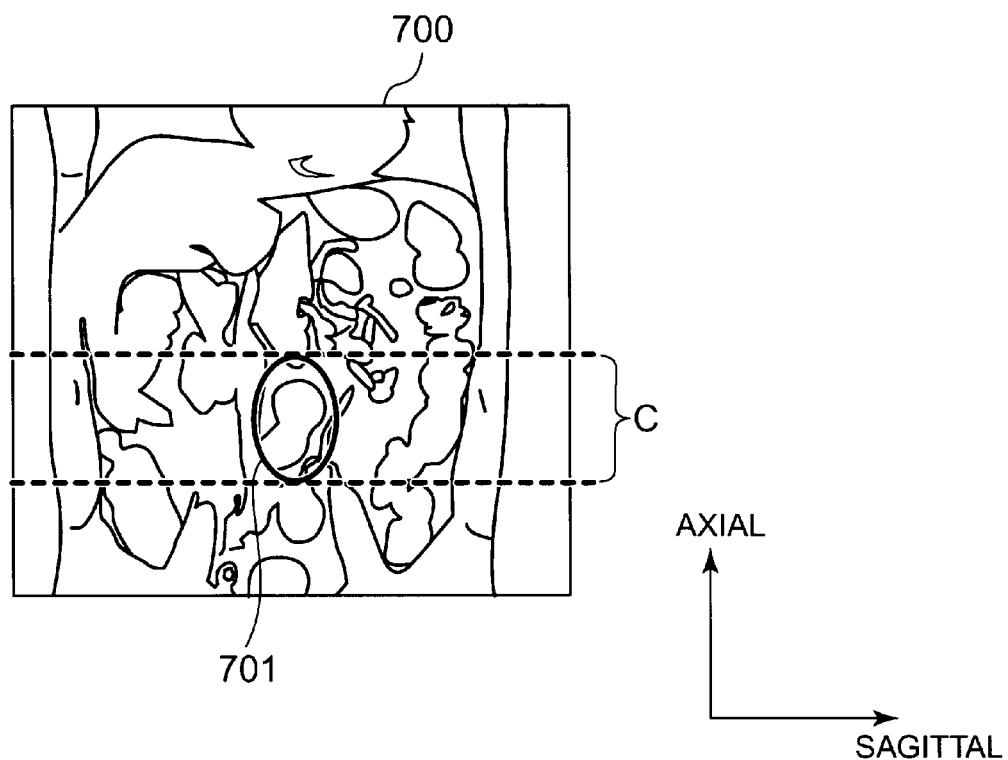
FIG. 10A is a diagram illustrating a key image of a previous examination.
Figure 10B:
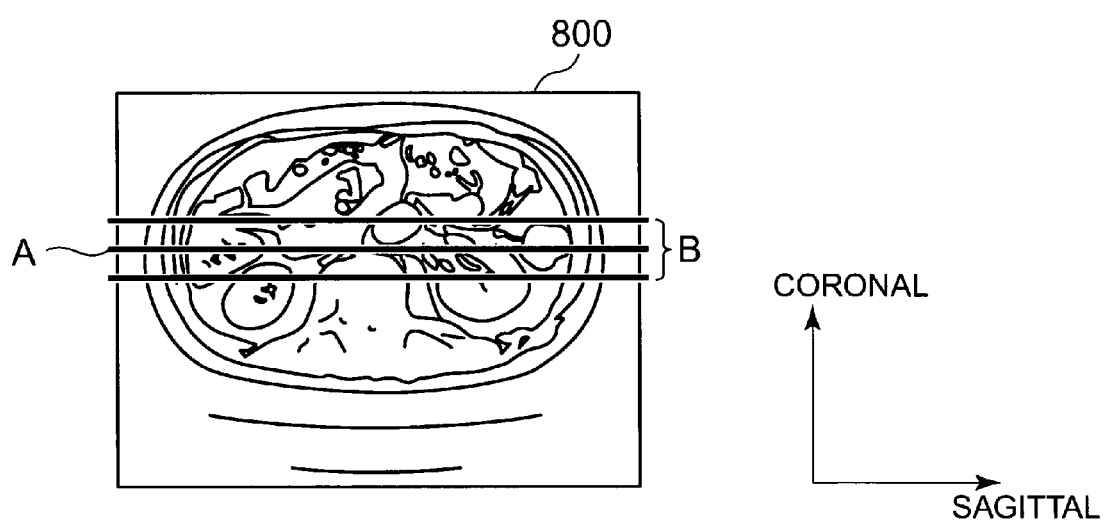
FIG. 10B is a diagram illustrating a medical image of a new examination.

Moreover, a specific site may be designated by key image data with an annotation. For example, a site to be focused is designated using an annotation. The designation of a specific site using an annotation is performed, for example, in the medical image-imaging apparatus 400. Herein, a case in which a specific site is designated with an annotation in a key image is described with reference to FIG. 10A, FIG. 10B, and FIG. 11. FIG. 10A is a diagram illustrating a key image of a previous examination. FIG. 10B is a diagram illustrating a medical image of a new examination. FIG. 11 is a diagram illustrating a frame format for describing a range in which image data is to be extracted from medical image data of the new examination.

A key image 700 shown in FIG. 10A is a tomographic image acquired during the previous examination. In this example, the key image 700 is a coronal image captured from the coronal direction. In this key image 700, a specific part (site) is designated with an annotation 701. The position (coordinate) of an annotation 701 and shape and size of the annotation 701 in the key image 700 are added to the key image data as annotation information. The image-generating condition-extracting part 7 extracts information regarding image-generating conditions and information regarding imaging conditions from the additional information added to the key image data and further extracts the annotation information. The image-generating condition-extracting part 7 outputs the information regarding image-generating conditions and the annotation information to the image data-extracting part 11.

On the other hand, the medical image 800 shown in FIG. 10B is a tomographic image acquired during the new examination. In this example, the medical image 800 is an axial image captured from the axial direction.

The image data-extracting part 11 specifies a position that corresponds to the cross-sectional position of the key image 700 (coronal image) of the previous examination in the medical image 800 (axial image) of the new examination. In addition, the image data-extracting part 11 specifies the part that the annotation 701 added to the key image 700 shows in the medical image 800 of the new examination.

In the example shown in FIG. 10B, in the medical image 800 of the new examination, a position A is the position that corresponds to the cross-sectional position of the key image 700. The image data-extracting part 11 specifies the position of the medical image 800 based on the cross-sectional position of the key image 700. In addition, the image data-extracting part 11 specifies a range in which image data is to be extracted based on the readable volume of data of the medical image observation apparatus 100A. For example, as shown in FIG. 10B, the image data-extracting part 11 determines the position A that corresponds to the cross-sectional position of the key image 700 (coronal image) as the reference position and determines range B for processing that extends in the coronal direction in the medical image 800 (axial image) as the range in which the image data is to be extracted.

In addition, the image data-extracting part 11 specifies a part that the annotation 701 added to the key image 700 (coronal image) shows in the medical image 800 (axial image) of the new examination.

For example, in the key image 700, the image data-extracting part 11 specifies a range C that includes a part that extends in the axial direction and is specified by the annotation 701. In the example shown in FIG. 10A, the image data-extracting part 11 specifies range C that contacts the part specified by the annotation 701.

As stated above, the image data-extracting part 11 specifies the extraction range in the coronal direction based on range B and specifies the extraction range in the axial direction based on range C.

The image data-extracting part 11 then extracts image data included in range B and range C among the a plurality of sets of tomographic image data included in the new examination and outputs it to the transmitter/receiver 3.

For example, as shown in FIG. 11, when a plurality of sets of tomographic image data (axial image data) is acquired along a specific direction (axial direction) in one series of the new examination, the series includes medical images 800A-800N (axial image). The image data-extracting part 11 extracts the image data included in range B and range C respectively from each of the medical images 800A-800N.

To describe in more detail, the image data-extracting part 11 extracts medical image data included in range C that extends in the axial direction respectively from the medical images 800A-800N. In the example shown in FIG. 11, the image data-extracting part 11 extracts the medical images 800C-800M included in range C among the medical image 800A-800N. In addition, the image data-extracting part 11 extracts image data included in range B shown with diagonal lines respectively from the medical images 800C-800M included in range C. As the above, the image data-extracting part 11 extracts the image data included in range B and range C respectively from the medical images 800A-800N. The image data-extracting part 11 then outputs the image data included in range B and range C to the transmitter/receiver 3. The transmitter/receiver 3 sends the image data included in range B and range C to the medical image observation apparatus 100A.

The transmitter/receiver 102 of the medical image observation apparatus 100A receives the image data included in range B and range C sent by the medical image storage apparatus 1A. The controller 103 causes the storage 4 to store the image data included in range B and range C. The image-generator 105 then generates MPR image data at the cross-sectional position that corresponds to the cross-sectional position of the key image of the previous examination by performing MPR processing on the image data included in range B and range C. For example, the medical image storage apparatus 1A sends the image-generating conditions of the key image of the previous examination to the medical image observation apparatus 100A. The image-generator 105 of the medical image observation apparatus 100A generates MPR image data of the new examination that corresponds to the key image of the previous examination by performing MPR processing on the image data included in range B and range C according to the image-generating conditions of the previous examination. This MPR image data includes an image that corresponds to the part designated with the annotation 701. The controller 103 causes the displaying part of the user interface 101 to display the MPR image based on the MPR image data. In addition, the image-generator 105 may generate MPR image data in an arbitrary cross-section based on the image data included in range B and range C.

Furthermore, when medical image data such as tomographic image data is stored in the image data storage 5 as being compressed, the medical image observation apparatus 100A (client) needs to extract the received medical image data. Therefore, when medical image data is compressed, the image data-searching part 6 may control the capacity of the medical image data to be read from the image data storage 5 considering extraction performed by the medical image observation apparatus 100A. To be more precise, the load on the CPU of the medical image observation apparatus 100A is considerable when extraction is performed by the medical image observation apparatus 100A, so the processing ability of the CPU of the medical image observation apparatus 100A is taken into consideration. Moreover, the capacity of the storage 104 in which the medical image data is stored after extraction is considered. As above, the image data-searching part 6 controls the capacity of the medical image data to be read from the image data storage 5 according to the processing ability of the CPU of the medical image observation apparatus 100A and the capacity of the storage 104 in which the medical image data after extraction is stored. For example, based on the information that shows the readable volume of data sent by the medical image observation apparatus 100A, the image data-searching part 6 reads medical image data that corresponds to half of the capacity of the volume of data from the image data storage 5. As an example, when the medical image observation apparatus 100A can read 100 images as the volume of data, the image data-searching part 6 reads 50 images of medical image data, which corresponds to half of the amount from the image data storage 5. The transmitter/receiver 3 then sends the medical image data read by the image data-searching part 6 to the medical image observation apparatus 100A. The medical image data stored in the image data storage 5 is compressed, so the medical image observation apparatus 100A extracts the received medical image data and causes the displaying part to display an image based on the medical image data after extraction.

(Processes)

Next, a sequence of processes of the medical image observation system according to the second embodiment is described with reference to FIG. 12. FIG. 12 is a flow chart illustrating a sequence of movement of the medical image observation system according to the second embodiment of the present invention.

(Step S20)

First, an operator enters the patient ID of a patient for examination into the medical image observation apparatus 100A using the user interface 101 and further gives instructions for the reading tomographic image data included in the new examination.

The transmitter/receiver 102 then sends the patient ID and instructions for reading the tomographic image data to the medical image storage apparatus 1A.

(Step S21)

The data-volume determining part 106 of the medical image observation apparatus 100A then determines a volume of data of tomographic image data that the medical image observation apparatus 100A reads based on the free space of the storage 104 and the communication speed of the transmitter/receiver 102.

(Step S22)

The transmitter/receiver 102 then sends the patient ID and the instruction for reading the tomographic image data to the medical image storage apparatus 1A. In addition, the transmitter/receiver 2 sends information that shows the volume of data determined by the data-volume determining part 106 to the medical image storage apparatus 1A.

(Step S23)

The transmitter/receiver 2 of the medical image storage apparatus 1A receives the patient ID, the instruction for reading, and the information that shows the volume of data sent by the medical image observation apparatus 100A and sends the patient ID to the report storage apparatus 200.

(Step S24)

The transmitter/receiver 201 of the report storage apparatus 200 receives the patient ID sent by the medical image storage apparatus 1 and outputs the patient ID to the report-searching part 203. The report-searching part 203 acquires an interpretation report that contains retrieval information that matches the patient ID from the report storage 202 and outputs the interpretation report to the key image-searching part

204. This interpretation report corresponds to the interpretation report of a previous examination.

(Step S25)

The key image-searching part 204 extracts image link information (information regarding a storage position) of a key image embedded into the interpretation report of the previous examination.

Alternatively, the key image-searching part 204 extracts image ID of the key image embedded into the interpretation report of the previous examination.

(Step S26)

The transmitter/receiver 201 sends the image link information (information regarding a storage position) of the key image to the medical image storage apparatus 1A. Alternatively, the transmitter/receiver 201 sends the image ID of the key image to the medical image storage apparatus 1A.

(Step S27)

The transmitter/receiver 2 of the medical image storage apparatus 1A receives the image link information (information regarding a storage position) or the image ID sent by the report storage apparatus 200 and outputs the image link information or the image ID to the image data-searching part 6. The image data-searching part 6 reads medical image data (key image data) stored in a location that the image link information (information regarding a storage position) of the key image shows from the image data storage 5. Alternatively, the image data-searching part 6 acquires information regarding a storage position that corresponds to the image ID and reads tomographic image data (key image data) stored in a location that the information regarding a storage position shows from the image data storage 5. The image data-searching part 6 then outputs the read tomographic image data (key image data) to the image-generating condition-extracting part 7.

(Step S28)

The image-generating condition-extracting part 7 extracts the information regarding image-generating conditions of the previous examination from the additional information added to the key image data. The image-generating condition-extracting part 7 then outputs the extracted information regarding image-generating conditions of the previous examination to the image data-searching part 6, the determining part 10, and the image data-extracting part 11. Moreover, when the additional information of the key image data includes annotation information, the image-generating condition-extracting part 7 also extracts the annotation information and outputs it to the image data-extracting part 11. In addition, the image-generating condition-extracting part 7 extracts information regarding imaging conditions from the additional information added to the key image data and outputs the information regarding imaging conditions of the previous examination to the determining part 10.

Moreover, the image-generating condition-extracting part 7 extracts information regarding image-generating conditions and information regarding imaging conditions of the new examination from the additional information added to the tomographic image data of the new examination. The image-generating condition-extracting part 7 then outputs the extracted information regarding image-generating conditions and information regarding imaging conditions of the new examination to the determining part 10.

(Step S29)

The determining part 10 compares the information regarding image-generating conditions of the previous examination with the information regarding image-generating conditions of the new examination and determines whether tomographic image data of the new examination that corresponds to the key image data is available.

Furthermore, the determining part 10 compares the information regarding imaging conditions of the previous examination with the information regarding imaging conditions of the new examination and determines whether the imaged sites are the same. Similarly to the first embodiment, the processing is then completed when the imaged sites are not the same. Subsequent processes are continued when the imaged sites are the same.

(Step S30)

When tomographic image data of the new examination that corresponds to the key image data of the previous examination is available (Step S29, Yes), the image data-searching part 6 reads the tomographic image data of the new examination generated at the cross-sectional position that corresponds to the cross-sectional position of the key image data from the image data storage 5. The transmitter/receiver 2 then sends the tomographic image data to the medical image observation apparatus 100A. In addition, the image data-searching part 6 determines the cross-sectional position of the key image data as the reference position and anteroposteriorly reads an arbitrary number of sets of the tomographic image data from the image data storage 5 around the reference position. At that time, the image data-searching part 6 reads the tomographic image data of the new examination from the image data storage 5 according to the information that shows the readable volume of data sent by the medical image observation apparatus 100A. The transmitter/receiver 2 then sends the plurality of sets of tomographic image data of the new examination to the medical image observation apparatus 100A.

(Step S31)

On the other hand, when tomographic image data of the new examination that corresponds to the key image data of the previous examination is not available (Step S29, No), the image data-searching part 6 outputs the plurality of sets of tomographic image data of the new examination to the image data-extracting part 11.

(Step S32)

The image data-extracting part 11 determines whether annotation information has been extracted.

(Step S33)

When annotation information has been extracted (Step S32, Yes), the image data-extracting part 11, as shown in FIG. 10A, FIG. 10B, and FIG. 11, extracts image data included in range B determined with the cross-sectional position of the key image data as the reference position and range C specified with the annotation from the plurality of sets of tomographic image data of the new examination.

At this time, the image data-extracting part 11 determines the size of range B based on the readable volume of data of the medical image observation apparatus 100A.

(Step S34)

On the other hand, when annotation information has not been extracted (Step S32, No), the image data-extracting part 11 extracts image data included in range B determined with the cross-sectional position of the key image data as the reference position from the plurality of sets of tomographic image data of the new examination.

At this time, the image data-extracting part 11 determines the size of range B based on the readable volume of data of the medical image observation apparatus 100A.

(Step S35)

The transmitter/receiver 2 sends the image data of range B or the image data included in range B and range C extracted by the image data-extracting part 11 to the medical image observation apparatus 100A. At this time, the transmitter/receiver 2 sends information regarding image-generating conditions of the key image of the previous examination to the medical image observation apparatus 100A.

(Step S36)

In the medical image observation apparatus 100A, the image-generator 105 generates MPR image data of the new examination based on the image data of range B or the image data included in range B and range C. The image-generator 105 generates MPR image data of the new examination by performing MPR processing on the image data of range B or the image data included in range B and range C according to the information regarding image-generating conditions of the key image sent by the medical image storage apparatus 1A. Moreover, the image-generator 105 may generate MPR image data in an arbitrary cross-section based on the image data of range B or the image data included in range B and range C.

Moreover, when the MPR image of the previous examination and the MPR image of the new examination are compared and interpreted, the operator enters the image ID of the MPR image of the previous examination using the user interface 101. The medical image storage apparatus 1A sends the MPR image data of the previous examination that corresponds to the image ID to the medical image observation apparatus 100A. The controller 103 of the medical image observation apparatus 100 causes the displaying part of the user interface 101 to display the MPR image of the previous examination next to the MPR image of the new examination.

As stated above, only the medical image data that is necessary for a comparative interpretation can be sent to the medical image observation apparatus 100A by determining the range of the medical image data sent to the medical image observation apparatus 100A based on the cross-sectional position at which the key image data has been acquired and the range specified with the annotation. Thus, it is possible to reduce the amount of time required to transmit the medical image data, enabling more efficient interpretation, etc.

Moreover, large-capacity memory may not be provided in the medical image observation apparatus 100A.

Moreover, the volume of data of the medical image to be sent can be minimized by determining the volume of data of the medical image data to be sent to the medical image observation apparatus 100A based on the capacity of the memory provided with the medical image observation apparatus 100A and the communication speed in the network. Thus, it is possible to reduce the amount of time required to transmit the medical image data, enabling more efficient interpretation, etc. Moreover, large-capacity memory does not need to be provided in the medical image observation apparatus 100A.

Furthermore, in the abovementioned first embodiment and second embodiment, MIP image data or MinIP image data, etc., may be generated instead of generating the MPR image data of the new examination. Moreover, 3-dimensional image data that sterically shows a subject may be generated by performing volume rendering on the medical image data of the new examination.

Moreover, the medical image storage apparatus 1A may send the remaining medical image data of the new examination to the medical image observation apparatus 100A as well as the medical image data of the new examination sent to the medical image observation apparatus 100A. To be more precise, the transmitter/receiver 2 of the medical image storage apparatus 1A may send the remaining medical image data to the medical image observation apparatus 100A as well as the medical image data extracted by the image data-extracting part 11. For example, when the image data-extracting part 11 extracts the image data included in range B and range C and the transmitter/receiver 2 sends the extracted image data to the medical image observation apparatus 100A, the transmitter/receiver 2 may further send image data of the new examination that is not included in range B and range C to the medical image observation apparatus 100A. Specifically, the transmitter/receiver 2 may send the medical image data (remaining medical image data) of the new examination that has not been extracted by the image data-extracting part 11 to the medical image observation apparatus 100A.

For example, when there is a request from the medical image observation apparatus 100A (client) for transmission to the medical image storage apparatus 1, the transmitter/receiver 2 sends the medical image data of the new examination that has not been extracted by the image data-extracting part 11 to the medical image observation apparatus 100A.

Moreover, when the communication speed of the network N is slow, the transmitter/receiver 2 may send image data that has not been extracted to the medical image observation apparatus 100A after sending the image data extracted by the image data-extracting part 11.

Moreover, when the capacity of the storage 104 of the medical image observation apparatus 100A is limited, the controller 103 of the medical image observation apparatus 100A may move the medical image data stored in the storage 104 to another storage apparatus and subsequently request the medical image storage apparatus 1A via the transmitter/receiver 102 to send the image data that has not been extracted by the image data-extracting part 11. The transmitter/receiver 2 of the medical image storage apparatus 1A receives the request and sends the medical image data of the new examination that has not been extracted by the image data-extracting part 11 to the medical image observation apparatus 100A.

What is claimed is:

1. A medical image observation system, comprising:
   a report storage configured to store an interpretation report that at least includes patient-identifying information, examination-specifying information, and medical image-specifying information that specifies medical image data;
   a medical image storage configured to store the medical image data that includes image data and additional information regarding said image data that at least includes the patient-identifying information, the examination-specifying information, and the medical image-specifying information;
   a medical image data-specifying part configured to specify an interpretation report that includes patient-identifying information, based on said patient-identifying information specified by a display request for medical image data, and to specify the medical image data using the medical image-specifying information included in said specified interpretation report;
   a medical image data-reading part configured to read the medical image data from said medical image storage based on the additional information of said specified medical image data and the examination-specifying information specified by said display request; and
   a displaying part configured to display an image based on the image data included in said read medical image data,
   wherein said medical image storage is configured to receive, as a series, a plurality of sets of tomographic image data acquired along an arbitrary direction, and to store the plurality of sets of said tomographic image data so that the image-generating conditions that show the conditions under which said tomographic image data has been generated are included in said additional information, the image generating conditions including cross-sectional position information, directional information, and thickness information; and said medical image storage is configured to store said medical image data so that the image-generating conditions that show the conditions under which said image data has been generated are included in said additional information, said medical image data-reading part including an image-generating condition-extracting part configured to extract the image-generating conditions from the additional information of said specified medical image data; and an image-generator configured to read, from said medical image storage, the plurality of sets of tomographic image data included in the series specified, based on the patient-identifying information and the examination-specifying information specified by said display request, so as to generate new medical image data by performing image processing on the plurality of sets of the read tomographic image data included in said read medical image data according to the cross-sectional position information, the directional information, and the thickness information indicated by said extracted image-generating conditions; and said displaying part is configured to display the image based on the image data included in said new medical image data.

2. The medical image observation system according to claim 1, wherein said medical image storage is configured to store said medical image data so that the image-generating conditions that include the information that shows the position in a subject at which said image data has been acquired are included in said additional information, to receive as the series, the plurality of sets of tomographic image data acquired along said arbitrary direction, and to store the plurality of sets of said tomographic image data so that the image-generating conditions that include the information that shows the position in the subject at which said tomographic image data has been acquired are included in said additional information; and said image-generator is configured to read from said medical image storage the plurality of sets of tomographic image data included in the series specified based on the patient-identifying information and the examination-specifying information specified by said display request, so as to generate said new medical image data by performing the image processing on a plurality of sets of tomographic image data included in a predetermined range among the plurality of sets of said read tomographic image data so that the position at which said specified medical image data has been acquired is defined as the reference position, the image processing being performed according to said extracted image-generating conditions.

3. The medical image observation system according to claim 1, wherein said medical image storage is configured to store the medical image data so that the image-generating conditions that include information that shows the position in the subject at which said image data has been acquired are included in said additional information;

said medical image data-reading part is configured to read medical image data included in a predetermined range that includes the position at which said specified medical image data has been acquired among a plurality of sets of medical image data specified based on the patient-identifying information and the examination-specifying information specified by said display request; and said displaying part is configured to display the image based on the image data included in said read medical image data.

4. The medical image observation system according to claim 3, wherein said image-generating conditions further include information that shows the direction in which said image data has been acquired, and said image data-reading part is configured to read medical image data included in said predetermined range so that the position at which said specified medical image data has been acquired is defined as the reference position when a plurality of sets of medical image data specified based on the patient-identifying information and the examination-specifying information specified by said display request includes medical image data acquired in a same direction as the direction in which said specified medical image data has been acquired.

5. The medical image observation system according to claim 4, wherein said medical image storage is configured to store the plurality of sets of tomographic image data so that image-generating conditions that include information that shows the position and the direction at and in which said tomographic image data has been generated are included in said additional information; and said medical image data-reading part is configured to read tomographic image data included in said predetermined range so that the position at which said specified medical image data has been acquired is defined as the reference position when a plurality of sets of tomographic image data specified based on the patient-identifying information and the examination-specifying information specified by said display request includes tomographic image data acquired in the same direction as the direction in which said specified medical image data has been acquired.

6. The medical image observation system according to claim 3, wherein said image-generating conditions further include information that shows the direction in which said image data has been acquired; and when a plurality of sets of medical image data specified based on the patient-identifying information and the examination-specifying information specified by said display request does not include medical image data acquired in the same direction as the direction in which said specified medical image data has been acquired, said medical image data-reading part is configured to specify a position at which said specified medical image data has been acquired in a plurality of sets of medical image data specified based on the patient-identifying information and the examination-specifying information specified by said display request and to extract image data included in said predetermined range that includes the specified position from each set of medical image data, and said displaying part is configured to display the image based on said extracted image data.

7. The medical image observation system according to claim 6, wherein said medical image storage is configured to store the plurality of sets of tomographic image data so that the image-generating conditions that include information that shows the position and the direction at and in which said tomographic image data has been generated are included in the additional information; and when a plurality of sets of medical image data specified based on the patient-identifying information and the examination-specifying information specified by said display request does not include tomographic image data acquired in the same direction as the direction in which said specified medical image data has been acquired, said medical image storage is configured to specify a position at which said specified medical image data has been acquired in a plurality of sets of medical image data that is specified based on the patient-identifying information and the examination-specifying information specified by said display request and to extract image data included in said predetermined range that includes the specified position from each set of tomographic image data.

8. The medical image observation system according to claim 7, wherein when a specific range is designated in said specified medical image data, said image data-reading part is configured to specify a position at which said specified medical image data has been acquired in a plurality of sets of tomographic image data specified based on the patient-identifying information and the examination-specifying information specified by said display request and to extract image data included in said predetermined range that includes the specified position and said specified range from each set of the tomographic image data.

9. The medical image observation system according to claim 3 further comprising:

a storage configured to store the medical image data read by said medical image data-reading part; and a data-volume determining part configured to determine a capacity of the medical image data read from said medical image storage based on a capacity of said storage and a communication speed between said storage and said medical image data-reading part, wherein said medical image data-reading part is configured to read image data with the capacity determined by said data-volume determining part as an upper limit.

* * * * *